United States Patent
Zasowski et al.

(10) Patent No.: US 10,546,653 B2
(45) Date of Patent: Jan. 28, 2020

(54) SYSTEMS AND METHODS FOR DETERMINING INSUFFICIENT MEDICAL DOCUMENTATION

(71) Applicant: 3M INNOVATIVE PROPERTIES COMPANY, St. Paul, MN (US)

(72) Inventors: Jeremy M Zasowski, Cambridge, MA (US); David R Bacon, Sandy, UT (US); Keith C Mitchell, Atlanta, GA (US); William L Schofield, III, Silver Spring, MD (US)

(73) Assignee: 3M Innovative Properties Company, Saint Paul, MN (US)

( * ) Notice: Subject to any disclaimer, the term of this patent is extended or adjusted under 35 U.S.C. 154(b) by 618 days.

(21) Appl. No.: 14/771,872

(22) PCT Filed: Feb. 28, 2014

(86) PCT No.: PCT/US2014/019212
§ 371 (c)(1),
(2) Date: Sep. 1, 2015

(87) PCT Pub. No.: WO2014/134378
PCT Pub. Date: Sep. 4, 2014

(65) Prior Publication Data
US 2016/0012187 A1    Jan. 14, 2016

Related U.S. Application Data

(60) Provisional application No. 61/771,618, filed on Mar. 1, 2013, provisional application No. 61/771,609, filed on Mar. 1, 2013.

(51) Int. Cl.
*G16H 10/60*     (2018.01)
*G06F 16/93*     (2019.01)
(Continued)

(52) U.S. Cl.
CPC .............. *G16H 10/60* (2018.01); *G06F 16/93* (2019.01); *G06F 19/3418* (2013.01); *G16H 50/20* (2018.01)

(58) Field of Classification Search
CPC ...... G06F 19/322; G06F 19/345; G06F 16/93; G06F 19/3418; G16H 10/60; G16H 50/20; G06Q 10/10; G06Q 50/22
See application file for complete search history.

(56) References Cited

U.S. PATENT DOCUMENTS

| 5,319,543 A | 6/1994 | Wilhelm |
|---|---|---|
| 6,915,254 B1 | 7/2005 | Heinze |

(Continued)

FOREIGN PATENT DOCUMENTS

| WO | 2014-134374 | 9/2014 |
|---|---|---|
| WO | 2015-126859 | 8/2015 |

OTHER PUBLICATIONS

Rosenbloom, "Interface Terminologies: Facilitating Direct Entry of Clinical Data Into Electronic Health Record Systems", Journal of the American Medical Informatics Association, 2006, vol. 13, No. 3, pp. 277-288.

(Continued)

*Primary Examiner* — Christopher L Gilligan
(74) *Attorney, Agent, or Firm* — 3M Innovative Properties Company; Jonathan V. Sry

(57) ABSTRACT

This disclosure describes systems, devices, and techniques for automatically identifying missing or ambiguous information in documentation associated with a patient. For example, a system may include one or more computing devices configured to receive documentation comprising a plurality of documented items related to the patient and determine, based on at least a subset of the plurality of documented items, one or more undocumented items missing from the documentation, wherein the subset of the (Continued)

plurality of documented items and at least one of the one or more undocumented items define a medical concept. The one or more computing devices may also be configured to generate, based on the one or more undocumented items, a code representative of the one or more undocumented items and output the code.

21 Claims, 31 Drawing Sheets

(51) Int. Cl.
*G16H 50/20* (2018.01)
*G06F 19/00* (2018.01)

(56) References Cited

U.S. PATENT DOCUMENTS

| | | | |
|---|---|---|---|
| 8,321,241 | B1 | 11/2012 | Mansour |
| 2002/0128861 | A1* | 9/2002 | Lau ................. G06Q 50/22 705/2 |
| 2004/0172297 | A1* | 9/2004 | Rao ................. G06F 19/328 705/2 |
| 2006/0087674 | A1 | 4/2006 | Lusen |
| 2009/0099871 | A1 | 4/2009 | Gadodia |
| 2011/0301966 | A1* | 12/2011 | Kartoun ............. G06F 17/274 705/2 |
| 2011/0301982 | A1 | 12/2011 | Green, Jr. |
| 2012/0078837 | A1 | 3/2012 | Bagchi et al. |
| 2012/0215551 | A1* | 8/2012 | Flanagan ........... G06Q 10/10 705/2 |
| 2012/0304054 | A1 | 11/2012 | Orf |
| 2012/0323598 | A1 | 12/2012 | Koll et al. |
| 2012/0329015 | A1* | 12/2012 | Thesman ........... G06Q 10/101 434/219 |
| 2013/0080187 | A1* | 3/2013 | Bacon ............... G06Q 50/24 705/3 |
| 2013/0262364 | A1* | 10/2013 | Verbeek ............. G06N 5/04 706/46 |

OTHER PUBLICATIONS

International Search Report for PCT International Application No. PCT/US2014/019212 dated Jun. 12, 2014, 2 pgs.

* cited by examiner

SYSTEMS AND METHODS FOR DETERMINING INSUFFICIENT MEDICAL DOCUMENTATION

CROSS REFERENCE TO RELATED APPLICATIONS

This application is a national stage filing under 35 U.S.C. 371 of PCT/US2014/019212, filed Feb. 28, 2014, which claims priority to U.S. Application No. 61/771,618 and U.S. Application No. 61/771,609, filed Mar. 1, 2013, the disclosures of which are incorporated by reference in their entirety herein.

TECHNICAL FIELD

This disclosure relates to systems and techniques for managing medical documentation.

BACKGROUND

When a physician interacts with a patient in a hospital setting, the physician will typically memorialize the encounter, usually by typing or dictation. The physician may memorialize the condition of the patient, the treatment plan, any services provided to the patient for treatment, etc. The resultant encounter-related documentation is reviewed by documentation review specialists, who read through the encounter-related documentation. If the specialists discover issues or problems in the encounter-related documentation and need clarification from the physician, the specialists may call the physician and leave the physician a message or email the physician regarding the issue. Upon patient discharge, the encounter-related documentation is reviewed by professional coders who may also discover issues and seek clarification from the physician, often using telephone or email communications.

SUMMARY

In general, this disclosure describes systems and methods for automatically identifying missing or ambiguous information in documentation associated with a patient. The systems and methods described herein may then provide one or more queries that solicit a physician to address the missing or ambiguous information. Depending on the type of issue identified in the documentation (e.g., missing or ambiguous information from the documentation), the system may generate the physician query to take the form of a multiple choice question or, for example, a response document that allows the physician to enter free form text. The systems and methods may update the documentation or other medical information in response to receiving user input associated with the query. In addition, the systems and methods may be configured to generate a list of potential medical problems from encounter-related information and update the list based on user input.

In one example, this disclosure describes a computer-implemented method for determining insufficient medical information associated with a patient, the method including receiving, by a computing device, documentation comprising a plurality of documented items related to the patient, determining, by the computing device and based on at least a subset of the plurality of documented items, one or more undocumented items missing from the documentation, wherein the subset of the plurality of documented items and at least one of the one or more undocumented items define a medical concept, generating, by the computing device and based on the one or more undocumented items, a code representative of the one or more undocumented items, and outputting, by the computing device, the code.

In another example, this disclosure describes a computerized system for coding medical documentation, the system including one or more computing devices configured to receive documentation comprising a plurality of documented items related to the patient, determine, based on at least a subset of the plurality of documented items, one or more undocumented items missing from the documentation, wherein the subset of the plurality of documented items and at least one of the one or more undocumented items define a medical concept, generate, based on the one or more undocumented items, a code representative of the one or more undocumented items, and output the code.

In an additional example, this disclosure describes a computer-readable storage medium including instructions that, when executed, cause one or more processors to receive documentation comprising a plurality of documented items related to the patient, determine, based on at least a subset of the plurality of documented items, one or more undocumented items missing from the documentation, wherein the subset of the plurality of documented items and at least one of the one or more undocumented items define a medical concept, generate, based on the one or more undocumented items, a code representative of the one or more undocumented items, and output the code.

In an additional example, this disclosure describes a computer-implemented method for requesting medical information associated with a patient, the method including receiving, by a computing device, a code representative of one or more undocumented items determined from a plurality of documented items related to the patient, generating, by the computing device and based on the code, a query that solicits user input addressing the one or more undocumented items, and outputting, by the computing device and for display, the query.

In an additional example, this disclosure describes a computerized system for requesting medical documentation associated with a patient, the system including one or more computing devices configured to receive a code representative of one or more undocumented items determined from a plurality of documented items related to the patient, generate, based on the code, an query that solicits user input addressing the one or more undocumented items, and output, for display, the query.

In an additional example, this disclosure describes a computer-readable storage medium including instructions that, when executed, cause one or more processors to receive a code representative of one or more undocumented items determined from a plurality of documented items related to the patient, generate, based on the code, an query that solicits user input addressing the one or more undocumented items, and output, for display, the query.

In an additional example, this disclosure describes a computer-implemented method for managing medical documentation associated with a patient, the method including receiving, by a computing device, user input responsive to a query presented via a user interface, wherein the user input addresses one or more undocumented items related to the query and determined from a plurality of documented items related to the patient, responsive to receiving the user input, generating, by the computing device, updated information indicative of the user input and related to the patient, generating, by the computing device, indicia indicative of the user input, and outputting, for display, the indicia.

In an additional example, this disclosure describes a computerized system for managing medical documentation associated with a patient, the system including one or more computing devices configured to receive user input responsive to a query presented via a user interface, wherein the user input addresses one or more undocumented items related to the query and determined from a plurality of documented items related to the patient, responsive to receiving the user input, generate updated information indicative of the user input and related to the patient, generate indicia indicative of the user input, and output, for display, the indicia.

In an additional example, this disclosure describes a computer-readable storage medium including instructions that, when executed, cause one or more processors to receive user input responsive to a query presented via a user interface, wherein the user input addresses one or more undocumented items related to the query and determined from a plurality of documented items related to the patient, responsive to receiving the user input, generate updated information indicative of the user input and related to the patient, generate indicia indicative of the user input, and output, for display, the indicia.

In an additional example, this disclosure describes a computer implemented method of managing medical information associated with a patient, the method including identifying, by a computing device, one or more potential medical problems with the patient from encounter-related information associated with the patient, generating, by the computing device, a list comprising the one or more potential medical problems, outputting, by the computing device and for display, the list, receiving, by the computing device, an indication of selection input from a user and associated with at least one of the potential medical problems, and updating, by the computing device, the list of potential medical problems according to the indication of the selection input.

In an additional example, this disclosure describes a computerized system for managing medical information associated with a patient, the system including one or more computing devices configured to identify one or more potential medical problems with the patient from encounter-related information associated with the patient, generate a list comprising the one or more potential medical problems, output, for display, the list, receive an indication of selection input from a user and associated with at least one of the potential medical problems, and update the list of potential medical problems according to the indication of the selection input.

In an additional example, this disclosure describes a computer-readable storage medium including instructions that, when executed, cause one or more processors to identify one or more potential medical problems with the patient from encounter-related information associated with the patient, generate a list comprising the one or more potential medical problems, output, for display, the list, receive an indication of selection input from a user and associated with at least one of the potential medical problems, and update the list of potential medical problems according to the indication of the selection input.

The details of one or more examples of the described systems, devices, and techniques are set forth in the accompanying drawings and the description below.

BRIEF DESCRIPTION OF DRAWINGS

FIG. 2 is an illustration of an example user interface that includes information from an electronic health record (EHR) of a patient.

Figure 3:
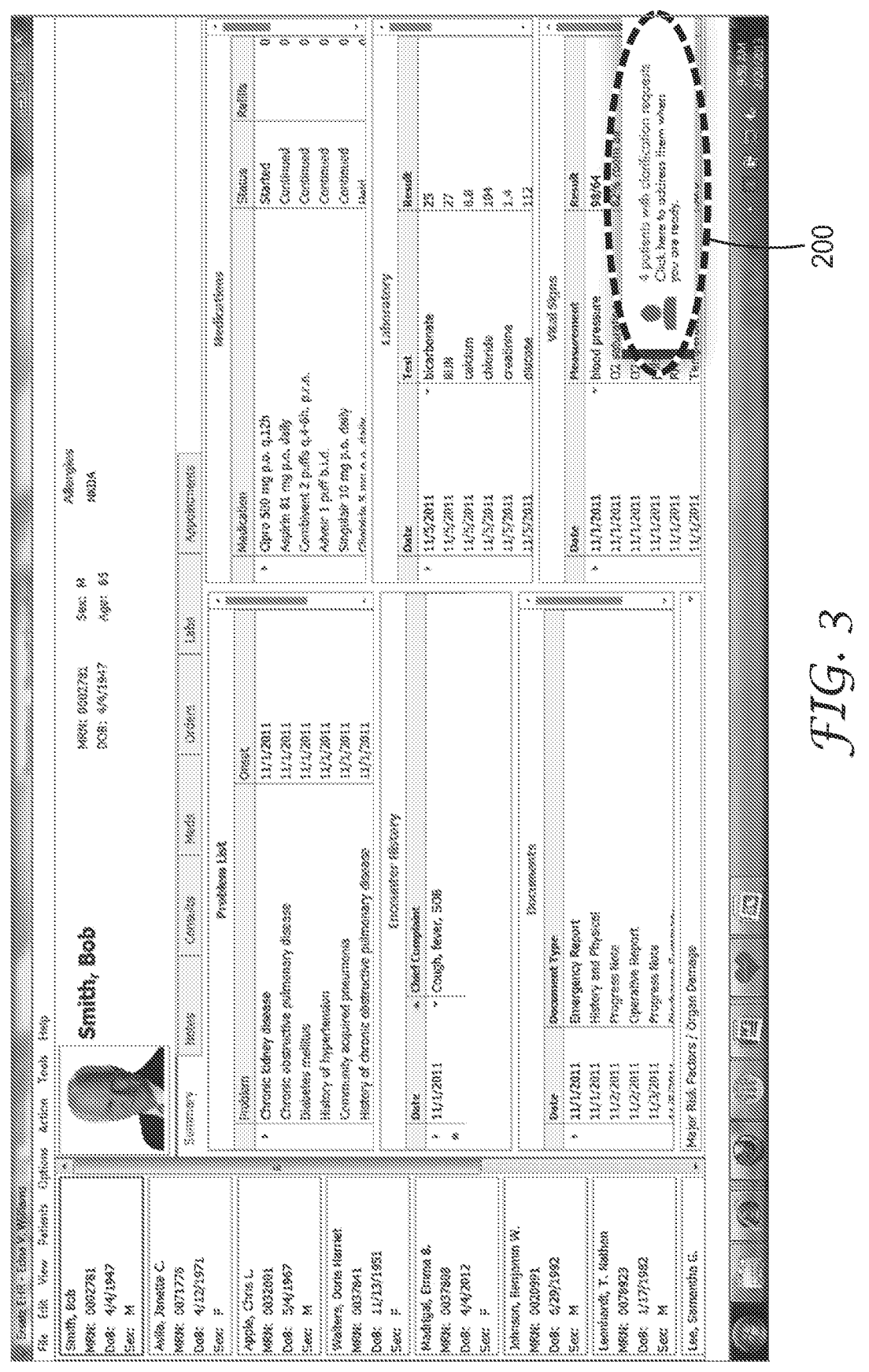

FIG. 3 is an illustration of an example user interface that indicates outstanding queries for a physician.

Figure 4:
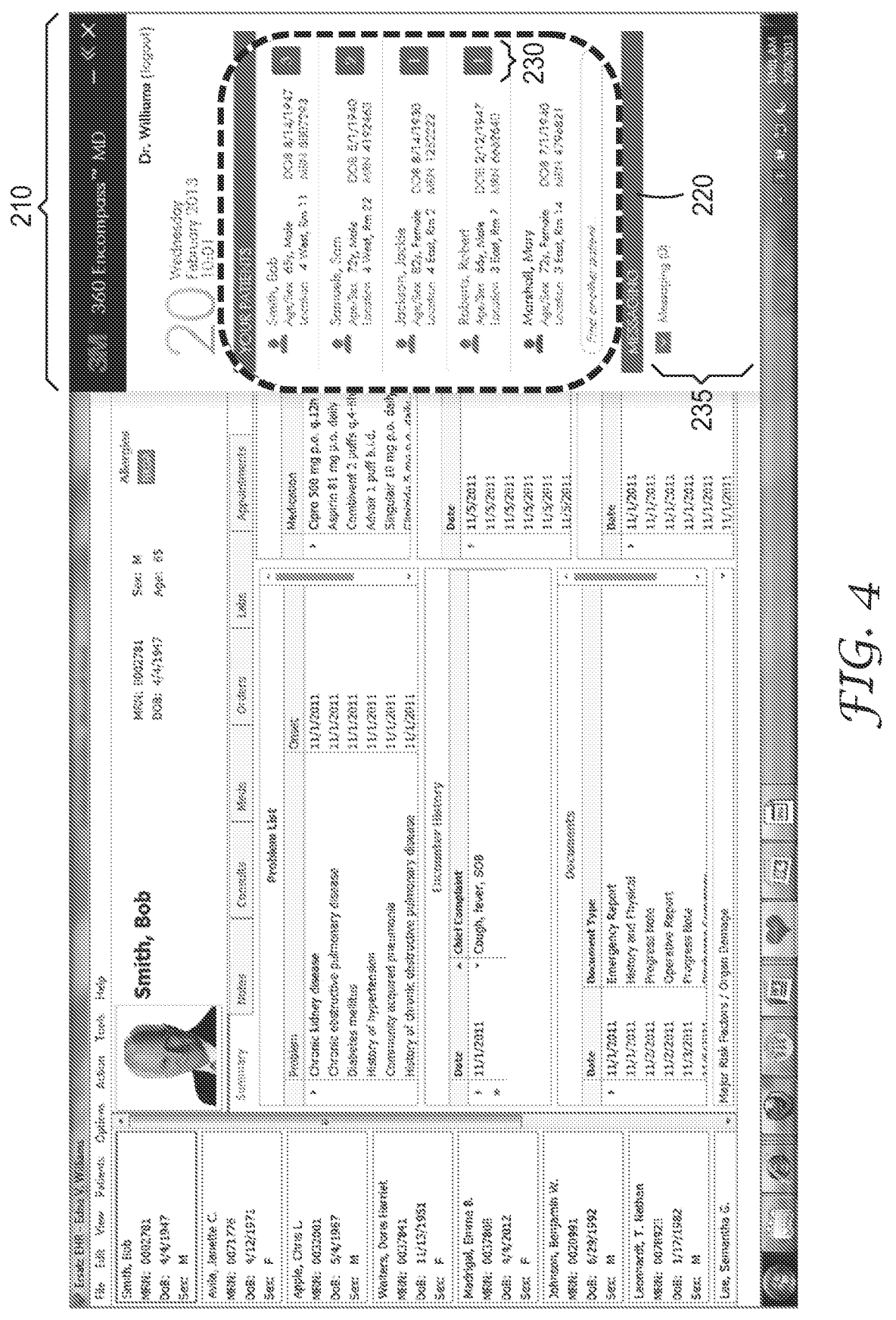

FIG. 4 is an illustration of an example user interface that indicates outstanding queries for each patient of a physician.

FIG. 5 is an illustration of an example user interface that presents queries to be addressed.

FIG. 6 is an illustration of an example user interface that presents selectable items for addressing an outstanding query.

FIG. 7 is an illustration of an example user interface that shows user input selecting a selectable item for a query.

FIG. 8 is an illustration of an example user interface that presents selectable items for addressing an outstanding query.

FIG. 11 is an illustration of an example user interface that includes a list of potential medical problems for a patient.

FIG. 12 is an illustration of an example user interface for updating a list of potential medical problems.

FIG. 13 is an illustration of an example user interface that includes an updated list of potential medical problems based on user input.

FIG. 14 is an illustration of an example user interface that includes outstanding queries for a patient.

FIG. 15 is an illustration of an example user interface that includes selectable items to address a query.

FIG. 16 is an illustration of an example user interface that shows user input selecting one of the selectable items of a query.

FIG. 17 is an illustration of an example user interface that shows another query regarding the same patient of FIG. 14.

FIG. 18 is an illustration of an example user interface that includes selectable items to address a query.

FIG. 19 is an illustration of an example user interface that includes documentary evidence relevant to a presented query.

FIG. 20 is an illustration of an example user interface that shows another query regarding the same patient as FIG. 14.

FIG. 21 is an illustration of an example user interface that includes a response document that accepts user input in the form of text.

FIG. 22 is an illustration of an example user interface that includes the user input within the response document provided in the example of FIG. 21.

DETAILED DESCRIPTION

Figure 1A:
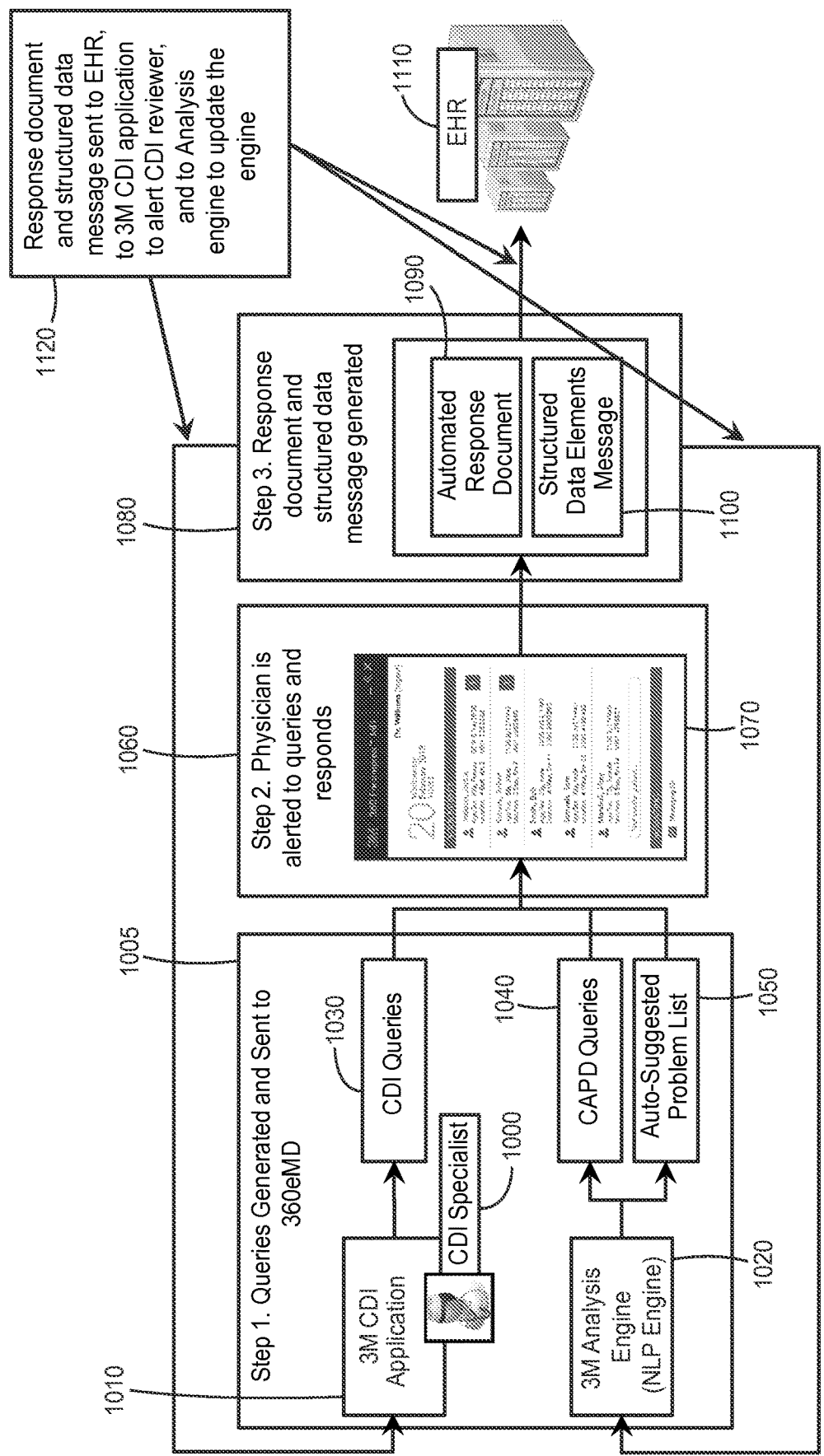
FIG. 1A is a flow diagram illustrating an example process for generating and presenting queries to a physician consistent with this disclosure.

This disclosure describes systems and techniques for managing medical documentation. A patient's encounter with a healthcare organization is usually initially documented by an attending physician, or by an emergency department physician in the emergency department, who may dictate the patient's condition, treatments, etc. In some examples the documentation may be created at the direction of the physician. Dictation related to the patient encounter, and other encounter-related documentation (e.g., hand-written or typed documents), may then be converted into billing codes through some type of coding process. The coding process is typically either done automatically using natural language processing algorithms or by professional coders reviewing the encounter-related documentation (or some combination of automated algorithms and manual coding).

The encounter-related documentation may also be used to update what is known as an electronic health record (EHR) (also known as an electronic medical record). Most hospitals have an EHR system that contains EHRs for patients associated with the hospital or clinic. The EHR may include the information about each patient, in digital format. EHRs may contain the medical record for the patient; however, the information contained in the EHR for each patient is usually spread across multiple documents and reports. Thus, the EHR may lack a cohesive, validated, and updated summary of the patient, his or her conditions, or related treatments. An example of a cohesive view of the patient medical record may be seen as the patient's "problem list" which contains one or more diagnoses and issues that the patient is being treated for or has been treated for in the past. While EHRs typically include a problem list for each patient, the problem list is typically manually created by a physician. The process of manually populating a problem list is, thus, time consuming, often error prone, and not rigorously continued or maintained throughout the patient's course of treatment in a hospital or clinical setting (e.g., most problem lists can become incomplete and inaccurate over the course of monitoring and treatment). A physician may spend a significant amount of time reviewing EHRs, determining treatment plans, issuing orders, and documenting each of their patients.

Regardless of the type of coding process used (e.g., automatic or manual coding), requests for additional information may be presented to a care provider from time to time, usually the physician who is more familiar with the patient's condition and the care administered thereto. Such requests or questions are, within the field, termed queries, clarification requests, or clarifications (such requests are referred to as "queries" herein). The information received from the physician for a query may be used by a professional coder to manually update the medical record (e.g., EHR or other related documentation) for the patient and/or billing information in order to more accurately reflect the severity of the patient's condition, the risk of the patient dying, and/or the level of care provided to the patient.

There are two general types of queries: computer generated queries and specialist queries. Computer generated queries are auto-generated by reviewing encounter documentation for each patient and looking for missing or unclear information. Specialist queries, on the other hand, are created manually by a clinical documentation improvement (CDI) specialist. CDI specialists are usually former nurses who have a clinical/medical background but also understand medical coding/billing and know what information is missing in a patient's chart and how to ask the physician to add that information.

The systems and methods disclosed herein are examples designed to facilitate more efficient extraction of information from a physician (or other healthcare provider) to improve encounter-related documentation. This improved encounter-related documentation (e.g., medical documentation) may be used to generate more accurate EHRs and billing codes and reduce the time required to achieve the more accurate EHRs and billing codes when compared to existing systems.

As described herein, a system may determine missing or ambiguous information in medical documentation, generate and present a query that solicits user input addressing the missing information, receives user input addressing the missing information, generates updated information based on the user input, and/or updates medical documentation associated with the patient with the updated information. In one example, a system may be configured to receive documentation that includes a plurality of documented items related to a patient. Based on at least some of the documented items, the system may determine one or more undocumented items (e.g., missing or ambiguous information) missing from the documentation. Some of the documented items and the one or more undocumented items may collectively define a medical concept. Based on the determined undocumented items, the system may generate and output a code representative of the undocumented items.

The system may also generate a query based on the code. In response to receiving the code representative of the one or more undocumented items, the system may generate a query that solicits user input addressing the one or more undocumented items and output the query for display. The system may then present the query to the physician within a user interface, such as a medical documentation interface. The query may identify the possible missing information or ambiguous information. The query may have a list of selectable items that address the query, and the physician may select one (or more in some examples) of the selectable items to address the query. Responsive to receiving the user input addressing the query, the system may automatically generate updated information indicative of the user input and related to the patient. The system may generate indicia indicative of the user input, output the indicia for display, and/or update medical documentation (e.g., the EHR) associated with the patient with the medical documentation. In this manner, the system may clarify possible problems with the medical documentation with limited physician input or physician time.

In some examples, the system may manage medical information associated with a patient. For example, the system may analyze encounter-related information associated with a patient to identify one or more potential medical problems with the patient. The system may generate a list of the potential medical problems and output the list for display to the physician. These potential medical problems may be part of a "problem list" associated with the user. The system may also be configured to receive an indication of selection input from a user, the selection input associated with at least one of the potential medical problems, such selection input may rearrange the list of problems, add a problem, delete a problem, modify a problem, or otherwise modify the list. In response to receiving the selection input, the system may update the list of potential medical problems according to the indication of the selection input. In this manner, the list of potential medical problems may be confirmed and/or adjusted by the physician to generate a "problem list" without the physician needing to manually populate the list of problems.

FIG. 1A is a flow diagram illustrating an example process by which a physician may be presented with one of the two general types of queries according to examples described herein. There are three general functional modules that may be involved with the process for generating and presenting queries to a physician, which may include software modules implemented on a general purpose computer: (1) Query construction, via query construction module 1010; (2) presentation of the query to physician, via user interface module 1060; and (3) response to the new physician input, via response module 1080. Query construction, via query construction module 1010, includes two paths, automated (e.g., processes performed by a computing device) and manual (e.g., processes that include manual intervention by a Clinical Documentation Improvement (CDI) specialist 1000. The automated path may involve an NLP engine (1020) configured to develop (or generate) two general types of queries: Computer-Assisted Physician Documentation (CAPD) queries (1040) and auto-suggested problems (1050) (which may include potential medical problems associated with the patient).

CAPD Queries may be one part of Automated Clinical Documentation Improvement (ACDI). ACDI generally concerns using natural language processing (NLP) technology running (i.e., executing) on one or more computer systems to automatically identify gaps or issues in clinical documentation (e.g., undocumented items such as missing or ambiguous information), then auto-generating a query to prompt a physician to add additional content or modify previously provided content to a particular patient's case. Along with the generation of the query itself, the query may subsequently be presented to a physician and physician response to the query may be received by the computing system to update at least some information in a patient's case (e.g., medical documentation associated with the patient).

Figure 1B:
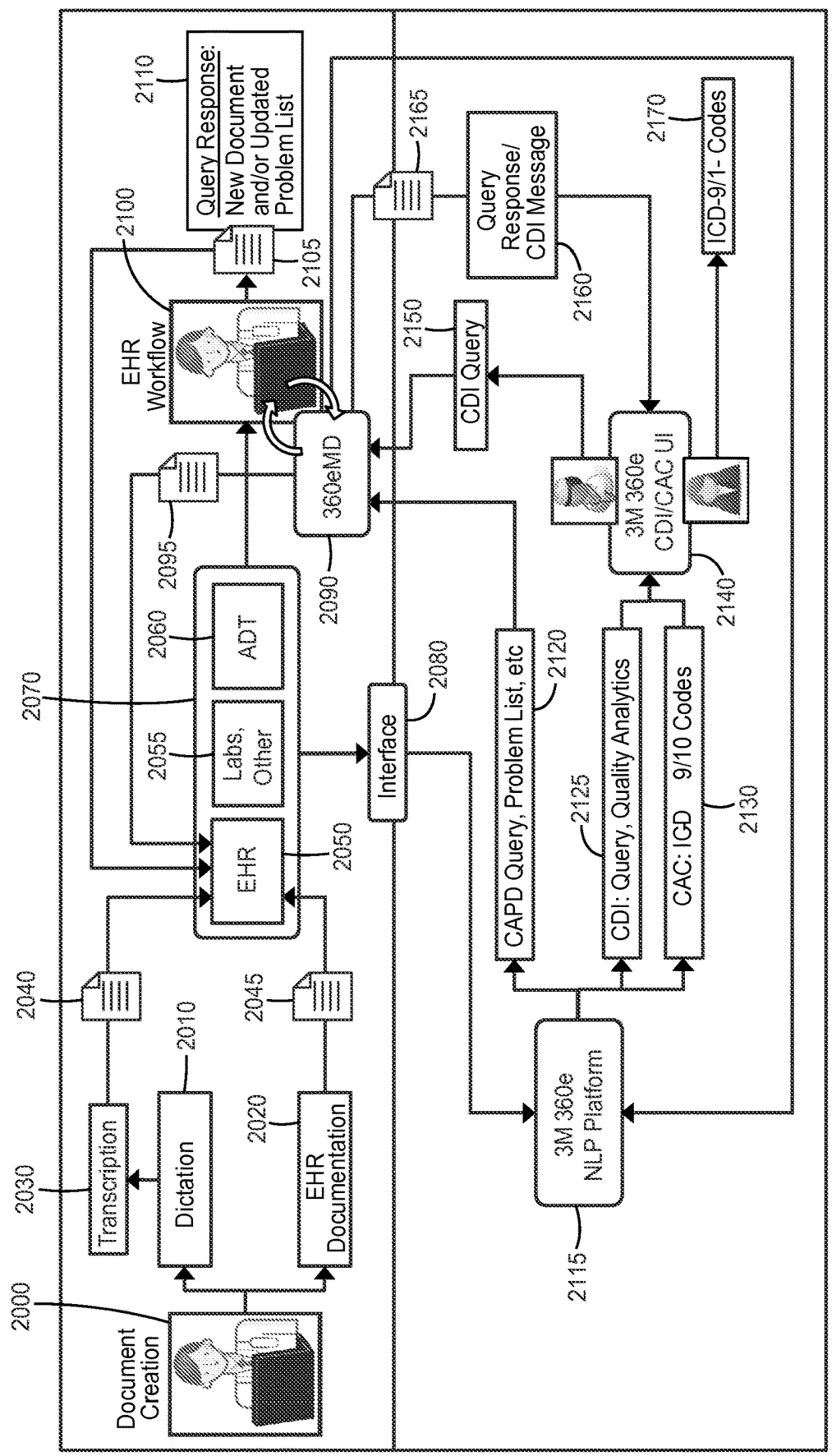
FIG. 1B is a flow diagram illustrating an example process for identifying missing or ambiguous information from medical documentation and generating associated queries consistent with this disclosure.
Figure 1C:
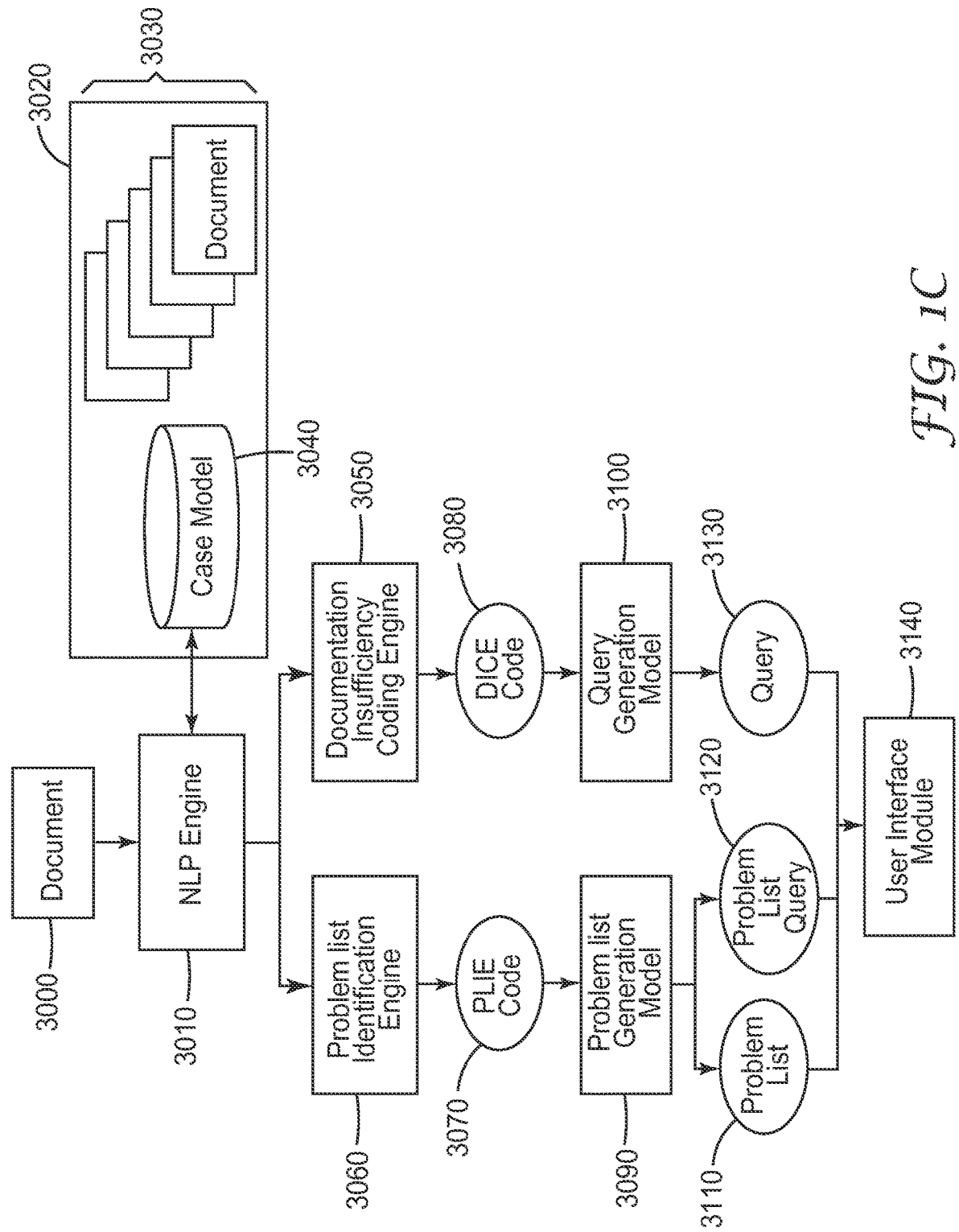
FIG. 1C is a flow diagram illustrating an example process for identifying missing or ambiguous information from medical documentation and generating associated queries consistent with this disclosure.

In reference to FIG. 1C, NLP analysis engine 3010 (an example of NLP engine 1020) may be configured to auto-generate CAPD queries which functions by first developing a "case model" for each patient visit. The case model 3040 may consist of all information, documentation and data available (data 3030) for a particular patient's visit or medical encounter. Data 3030 may include medical documentation associated with the patient. The NLP engine 3010 may be configured to analyze each new received document 3000 or component of data, such as laboratory or test results, and build a structured summary view of the patient for the case model 3040. This analysis from NLP engine 3010 may include identifying and tagging, within every document or data source, each diagnosis, symptom, vital sign, or other patient information, as well as each test, lab, or procedure performed. The NLP engine 3010 also determines whether each element in the case model is current for the visit or encounter, or whether each element is historical (i.e., from a past encounter), or is related to a familial history or linkage. Each relevant piece of information about this patient's current, historic, or familial medical history (e.g., documented items) may then be mapped by the NLP engine 3010 to a concept code called a concept identification code. The concept identification code is an intermediary code set that is mapped to and from other commonly used code sets. Each concept code may define or represent a medical concept. These common identifier codes for each patient, along with the relationships between the common identifier codes, are then stored in the case model 3040 as well.

The common identification codes are part of what is termed a healthcare data dictionary (HDD). Each of the concept identification codes is mapped, or linked, to most other available industry coding sets or terminology standards, such as International Classification of Diseases (ICD)-9 and ICD-10 codes or SNOMED-CT codes. Mapping every piece of information in a patient's medical record to a concept identification code, allows for ready translation of any one code or term, to any other code or term from another standard.

As new documentation (e.g., medical document 3000) is generated, NLP engine 3010 may process and map elements from document 3000 to clinical identification codes in the case model 3040. The resulting information is sent to a documentation insufficiency coding engine (DICE) 3050, which may be functionally implemented as a software module running on a computer system. The DICE 3050 performs the process of analyzing the information from document 3000 and clinical identification codes associated with the resulting documentation to establish relationships between the codes. The DICE 3050 may then follow a set of insufficient documentation coding rules to determine if any of the information or evidence contained within this document 3000 triggers generation of an insufficient documentation code 3080 (e.g., the presence or absence of an item results in an identified insufficiency).

The process of generating an insufficient documentation code 3080 may start with the analysis of the most recently submitted document; for example, document F. If the system determines that evidence is found within document F that meets the criteria for prompting a query, then the system marks a query for the document, along with noting the author (e.g., the physician) and patient and other relevant information about this patient and this encounter. The evidence is also linked to the query, so it may be referenced by the physician, as described below. Before this query is sent to a physician however, the DICE 3050 then references the case model 3040, documents A-E, to determine two other key items. The first item determined by DICE 3050 is whether evidence in this document 3000, which was insufficient to generate an insufficient documentation code on its own, would trigger an insufficient documentation code when combined with, or analyzed alongside information contained in the case model 3040. For example, evidence from document F combined with evidence from documents A and C may be sufficient for DICE 3050 to trigger an insufficient documentation code 3080. The second item determined is whether the DICE 3050 can validate that there is not information in the case model that would suppress or cancel the insufficient documentation code triggered documented items within document F. For example, document F may have triggered DICE 3050 to generate an insufficient documentation code 3080 for a type of heart failure; however, in document B which was previously submitted and now part of case model 3040, the type of heart failure may be fully defined as acute systolic heart failure—evidence that would suppress the insufficient documentation code triggered by document F because a fully defined diagnosis has already been made.

Once an insufficient documentation code is triggered and generated, DICE 3050 may send this code to the query construction module 3100, which contains a database of queries. The insufficient documentation code 3080 is matched to the corresponding query 3130 from the database of queries, and query 3130 is then sent via the interface module 3140 to the physician to solicit a response and resolution to the query 3130 (as shown below). The selected, or generated, query may take one of two forms, depending on the type of insufficient documentation code 3080 that is triggered.

A query may be of different forms or types of queries. One query form, called specificity queries, may include a specific question related to the documentary evidence which triggered the query, along with a set of multiple choice, pre-scripted responses (e.g., a list of selectable items) that the physician may choose from to respond to the query. A specificity query may be triggered when the documentation does not fully and completely define a diagnosis or procedure related to the patient. An example of a specificity query may be where documentation of "heart failure" does not adequately document whether or not the condition of heart failure is "acute" or "chronic."

Another query form, called a casual linkage query, may describe a situation where the facts documented for a patient indicate more specific diagnosis, but a more specific diagnosis has not been stated. The casual linkage query may typically occur when two or more separate facts in the documentation could be linked together to note a more specific and complete diagnosis, but the physician has not made the appropriate connection between those facts. An example of a casual linkage query may be where a diagnosis of pneumonia is documented and test results indicate there is pneumococcus in the patient's sputum, but the specific type of pneumonia, pneumococcal pneumonia, has not been documented.

A third query form, called clarification or underlying condition queries, may include a summation of the evidence that triggered the query, along with an open ended question that the physician must respond to with a text (typed using a keyboard or a speech recognition product) into a response document. The underlying condition query may occur when an underlying condition is indicated by clinical facts but the underlying condition or diagnosis is not stated in the documentation. An example underlying condition query may be where many of the clinical signs and symptoms of acute respiratory failure are documented (e.g., elevated respiratory rate, low oxygen blood levels, rales, tachycardia, and use of accessory muscles or breathing), but the diagnosis of "acute respiratory failure" has not been documented. The underlying condition query may be more closely related in form and response process to a specialist query, and the underlying condition query may be used when a there is evidence in the case model 3040 to suggest that the patient has a condition or diagnosis that the physician has not specifically documented.

For each query type or form, DICE 3050 may follow a different set of query rules and logic for analyzing all the documentation within case model 3040 and determining if one of the types of queries should be sent to a physician. The set of query rules may be dependent upon the type of information that must be identified and how that information may need to be analyzed. For example, for specificity queries, DICE 3050 may identify target diagnoses and then determine whether the appropriate information is also present in one of the documents in case model 3040 in order to fully specify the diagnosis. For casual linkage queries, DICE 3050 may identify one or more target diagnoses and then search for any "casual" information which could be linked to the target diagnoses. The casual information may be another diagnosis, a test or lab result, or a symptom or other condition which is associated with the patient. For underlying condition queries, DICE 3050 may identify key signs and symptoms in the documentation. These signs and symptoms may be test of lab results, vital signs, or a symptom or condition which is present in this patient for a particular patient visit. The key signs and symptoms may be grouped into sets and linked to one or more target diagnoses within the rules and logic. For each set of signs and symptoms, DICE 3050 may attempt to identify whether the corresponding target diagnosis is also documented. If DICE 3050 cannot find the target diagnosis within case model 3040, DICE 3050 may generate a code for a respective query.

The queries pulled (e.g., selected or generated) from the database may be formed properly so as to comply with industry standards. Thus, a professional coder may oversee the generation of the queries and responses that are populated into the database (which is accessed by the query generation module 3100). For example, if a physician has not already written a certain diagnosis into a document, and the diagnosis is not contained anywhere else within the medical record for the patient's current encounter, it may be considered an issue of non-compliance to suggest a specific new diagnosis through a query to a physician, per AHIMA (American Health Information Management Association) guidelines. This condition may necessitate an underlying condition query which facilitates an open ended answer to the posed question of the query.

However, if a certain diagnosis is already contained in the patient's medical record for the current visit, and the required information is that the physician more completely clarify the existing documented diagnosis, then DICE 3050 may determine that it is acceptable to present the physician with that diagnosis as well as a list of acceptable options (e.g., a list of selectable items) that completely define and detail the patient's specific condition when selected. Thus, it may be beneficial, or even necessary in some examples, to have multiple query forms to account for the different types of queries in the query construction module 1010 or query generation module 3100.

Specialist queries (also called Clinical Documentation Improvement Queries (CDI Queries)) may be similar to CAPD queries in that they are requests sent to a physician to clarify missing or unclear information about a patient. However, specialist queries are created manually by a clinical document improvement (CDI) specialist, i.e., a human professional. CDI specialists are typically former nurses who have a clinical/medical background but also understand medical coding/billing and know what information is missing in a patient's chart and how to ask the physician to add that information. Physicians then create a new document and answer the CDI specialist's query.

Referring back to FIG. 1A, the first path, starting with step 1010, utilizes a CDI application to interact with a CDI specialist 1000 to generate specialist queries (which are then presented to a user, usually a physician, in step 2). The second path, starting with NLP engine 1020, concerns automatically generated queries. The automatically generated queries may be CAPD queries, which were discussed above. Automatically generated queries may instead relate to problem lists 1050.

A problem list may be a set of medical information about a patient that summarizes the main problems, diagnoses, and issues that a patient is being treated for or that are associated with this patient's medical condition. According to the American Health Information Management Association (AHIMA), the problem list offers four benefits: (1) it enables more customized care through the identification of the patient's most important health information; (2) it can help identify "disease specific populations" through data analysis; (3) it can help evaluate standard measures for specific practitioners and health care organizations; and (4) it can identify patients for relevant research studies.

Problem lists are typically created and maintained manually by physicians. For example, the physician may type in the text to describe each of the problems in the problem list. The problem lists are usually stored and maintained as part of the healthcare facility's EHR. During the course of a patient's stay or treatment in a hospital or clinic, the items in the problem list may change as a condition worsens or improves: some problems may no longer be relevant, while some new problems may arise. Any updates or changes to the problem list typically requires a physician to exercise manual diligence and update the problem list. Two separate attending physicians may exercise differing levels of diligence regarding the updating of the problem list, and the problem list may become outdated or even inaccurate.

For creation of a proposed problem list (e.g., a list of possible medical problems) by the NLP engine according to embodiments described herein, the same process of creating a case model for the patient, as detailed previously in reference to FIG. 1C, may be followed. Also as detailed previously, the NLP engine 3010 maps all relevant patient information to clinical concept codes. These clinical concept codes as part of the case model 3040 and are then analyzed by a problem list identification engine (PLIE) 3060, which may be implemented as a software module on a computer system. The PLIE 3060 may follow a set of problem list rules to map the information in the case model 3040 and the concept identification codes to either SNOMED-CT codes, or to ICD-9 codes, or to ICD-10 codes (collectively, "problem list codes" 3070). At the time of system implementation (or later, if desired), the hosting organization's information technology department may configure which of the possible codes they wish to use for their organization's problem list. The problem list codes, once determined for the particular case model, are then sent to the problem list generation module 3090 that applies problem list rules to formulate these problem list codes into a proposed current problem list for problems that are being treated or are affecting the current patient encounter. Problem list generation module 3090 may also apply the problem list codes into a historical problem list which contains problems that are identified as being part of a past encounter, or part of the patient's past medical history.

The problem list generation module 3090, in one example, sends the current and historical problem lists to the interface module 3140 for presentation to the user physician, the newly identified problems taking the form of a suggested problem list (or query (3120)). The current problem list 3110 may also be displayed. The physician may use the historical problem list for reference in treating the patient on this current encounter, and the physician can choose to add problems from the historical problem list to the current problem list 3110. The physician is also able to review, edit (remove or add problems) to the current problem list 3110. Once the physician validates the current problem list, the validated current problem list may be used for inclusion in new documentation created in the interface module and may be exported to the EHR to update the official problem list as maintained in the patient's record within the patient's EHR.

Example systems described herein may be configured to review all documentation available for a patient's case and identify all relevant problems, diagnoses, and issues that a patient is being treated for, or that are associated with this patient's medical condition (herein referred to collectively as "problems"). These problems may, in some examples, be coded per standards consistent with the International Classification of Disease or other industry standards (for example, ICD-9, ICD-10, or SNOMED CT), and consistent with the notion of Meaningful Use as defined by the Health Information Technology for Economic and Clinical Health (HITECH) Act of 2009 and administered by the Centers for Medicare and Medicaid Services (CMS). Meaningful Use is related to the Medicare EHR Incentive Program which provides incentive payments to eligible professionals, eligible hospitals, and critical access hospitals (CAHs) that demonstrate meaningful use of certified EHR technology. Consistent with examples further described herein, these automatically identified problems (e.g., potential medical problems) are then presented to a healthcare provider though a graphical user interface to allow the provider to edit, validate, and approve the problem list. The approved problem list can then be exported to the healthcare facility's EHR.

Regardless of whether the query includes specialist queries (i.e., CDI queries 1030), CAPD queries (1040), or problem queries (1050), the queries may be constructed by a query construction module or query generation module 3100 to most effectively solicit missing or unclear information from the user (e.g., a physician). Query 1070 in FIG. 1A is an example query presented via user interface module 1060. The query construction module may access a database of questions and possible answers from a database containing pre-constructed questions and possible answers. The pre-constructed questions and possible multiple answers are developed by specialists to conform with industry standards (for example, the questions cannot be leading). As described earlier, the query related questions can take the form of specificity queries, which includes multiple choice response options (e.g., a list of selectable items), or underlying condition queries, which present triggering evidence and ask the physician to appropriately respond via free text input. Problem list queries may take the form of the initial problem list generation (e.g., potential medical problems) and ask the physician to edit if required, and then ultimately validate the NLP generated problem list.

New problems that are identified by the PLIE (e.g., PLIE 3070) during the course of the patient's encounter and sent to the physician as a problem list query to determine if the physician believes this new problem may also be validated and added to the existing problem list. Also, as specialist and/or CAPD queries are responded to (e.g., to either clarify an existing diagnosis making it more complete or adding a new diagnosis), the PLIE may process these query responses in the user interface module and problem list generation module to automatically update the current problem list. Once the query is constructed, the system is next presented to a physician or other provider via one or more user interfaces generated, at least in part, by user interface module 1060. Example user interfaces are further described below.

Response module 1080 may be configured to process the response from the physician received via user interface module 1060. Depending on the query type (specialist, CAPD, or problem), the response module 1080 may create two automated responses. The first response is the generation of an automated response document 1090 that includes a textual representation of the query and answer. The response document 1090 may be presented to the physician, who may then edit it as he or she feels is appropriate before electronically signing or otherwise validating the contents of response document 1090. The response document 1090 may then be associated with the patient's EHR which allows the new information in the response document to be communicated to other healthcare providers and members of the care team. As the new information in the response document 1090 is now part of the patient's EHR, the new information may also therefore be available for subsequent coding, billing, and reporting purposes.

If the query solicits user input to result in the updating of the patient's problem list, then the second automated response may be a structured data message 1100 or structure data package that results in the updating of discrete data elements in the patient's EHR. This message or package may take the form of an HL7 message (Health Level Seven International (HL7) is the global authority on standards for interoperability of health information technology and defines the structure of messages used for communication between healthcare IT systems to enable interoperability between systems) or CDA document (Clinical Document Architecture a standard format for structure healthcare documents to allow for interoperability between electronic systems), or any other format as specified by or supported by the EHR system. Since EHRs contain a number of discrete, structured data fields where important information about a patient is stored (for example, a problem list), it is important that these fields be updated when new information is generated about a patient or their treatment. By exporting the updated diagnoses and problems to the EHR, this allows these discrete data fields in the EHR to be updated automatically without requiring a physician or other healthcare provider to manually change or update this information. Thus patient's EHR may then be updated to reflect the newly garnered information in the EHR 1110. Any of the information generated from response module 1080, such as response document 1090, structured data elements message 1100, or any other information, may be used by the system to inform CDI specialist, module 1010, or NLP engine 1020 to update the processes used to determine missing information and/or generate queries.

FIG. 1B is a flow diagram illustrating an example process for identifying missing or ambiguous information from medical documentation and generating associated queries consistent with this disclosure. FIG. 1B shows the general workflow and data flows. The workflow of FIG. 1B begins with a physician or other healthcare provider creating documentation for a patient (2000). This documentation process may be done through dictation-transcription (2010, 2030) or by a physician entering information directly into an EHR (2020) to create a new document or to complete a template in an EHR. This process may result in new documentation or clinical notes (2040, 2045) that become part of the permanent medical record for that patient in the EHR. This information, along with information about the patient contained in other hospital systems (2070) such as laboratory data, test results or medications (2055) as well as patient admission, discharge and transfer (ADT) information (2060) is then sent via an interface (2080) to the application's NLP platform (2115). Any portion of this information received by the NLP platform may be considered medical documentation associated with the patient.

As part of the NLP-driven automated analysis process, all available information about a patient's case may be assembled into a multi-document view of the patient called a "case model" which may be described as a broad summary about that patient's case or history, and includes patient encounter-related information. From all of the information in the case model, a number of analyses may be performed which can result in multiple outputs, including CAPD queries, problem list suggestions (e.g., potential medical problems), (2120), specialist queries (i.e., CDI queries), as well as high-risk patient alerts (2125) ICD-9 codes, ICD-10 codes (2130), or any other type of information related to the patient.

The CAPD queries and problem list suggestions (2120) are then surfaced to the physician or other healthcare provider via the user interface module (2090). The specialist queries (CDI queries), ICD-9, ICD-10 codes and other analytics including high risk patient alerts are sent, in this example, to a separate user interface module (2140) for use by CDI specialists and coders as part of their workflows. However, all queries may be sent to the physician in other examples for resolution. CDI specialists, via user interface module (2140), may generate ICD-9, ICD-10 codes for use herein or by other systems (2170).

CDI reviewers can create specialist queries based on their manual analysis of the patient's case model and the information provided to them (2125, 2130) by the NLP platform (2115). These CDI queries are then sent by the user interface module (2140) to the physician user interface module (2090) to be presented to the physician and solicit physician response.

The physician may then interact with the user interface module (2090) making appropriate selections or responses to the queries presented (and further shown, below) by selecting from a multiple choice list for CAPD queries, adding a brief amount of text to an auto-generated response document for specialist queries, as well as updating and validating the auto-generated problem lists. In this manner, the physician responses to the queries may address undocumented items and/or potential medical problems associated with the patient.

The physician's response to a query may then result in the system creating automated response documents which, when validated or signed (2105, 2095, 2110) are sent to the EHR as a new, signed document as well as a structured data message to update the structured data fields in the EHR when appropriate. EHR Workflow 2100 may include the creation data for the EHR, based on inputs such as those inputs received from the user interface module (2090) and information from hospital systems (2070).

The resultant responses may also be sent back (2165, 2160) to the CDI specialist and coder user interface module (2140) to update the CDI specialist and provide the CDI specialist with real-time updates on physician responses. The CDI specialist may modify actions for future iterations based on the physician responses. The automated responses (not numbered in diagram) may also be sent back to the NLP platform (2115) for analysis to ensure that the physician's responses adequately answered the query and to update the case model for future analysis of the patient's case.

Figure 1D:
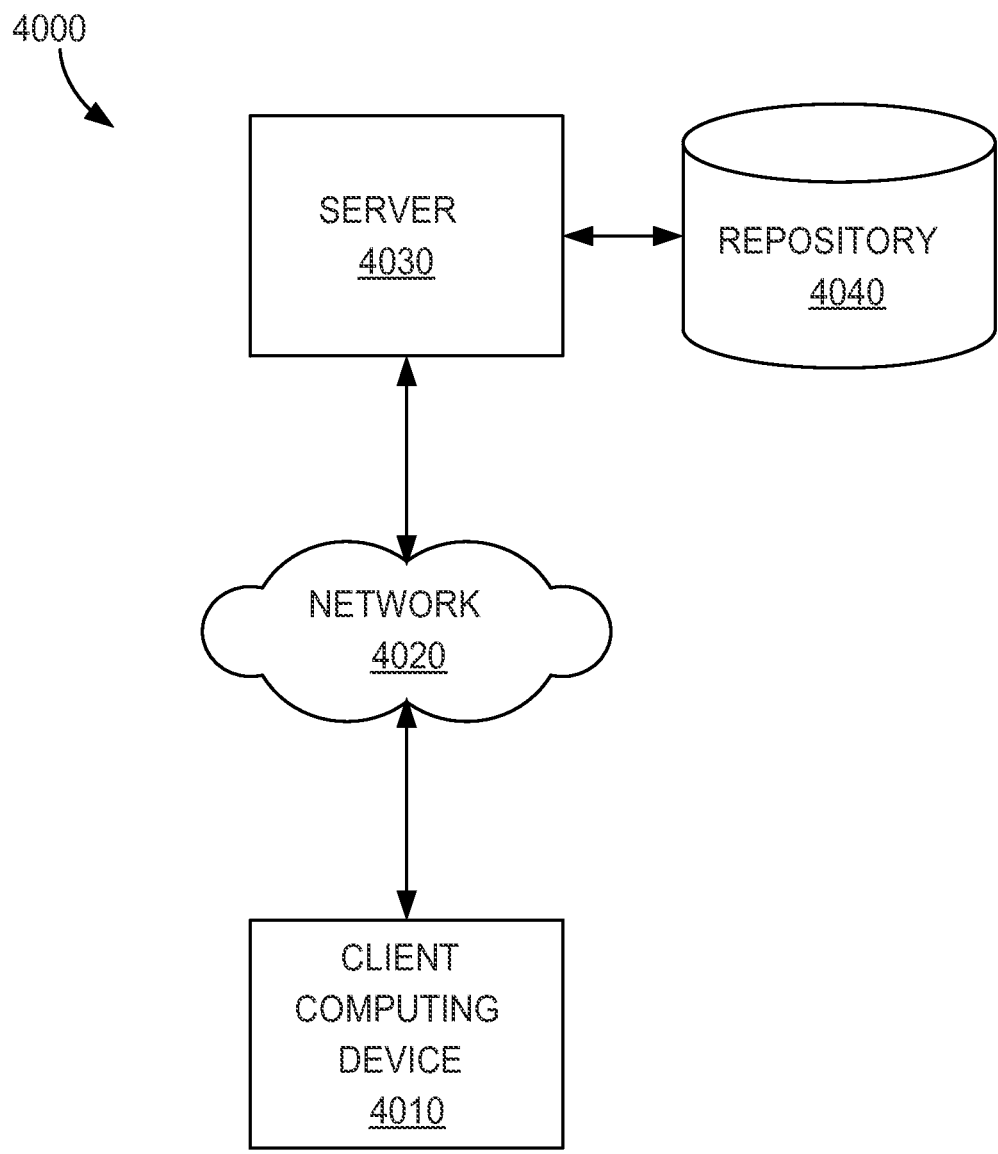
FIG. 1D is a block diagram illustrating an example system configured to analyze and manage medical documentation consistent with this disclosure.

FIG. 1D is a block diagram illustrating an example system 4000 configured to analyze and manage medical documentation consistent with this disclosure. System 4000 may include devices and components configured to perform the processes described herein, such as in the processes of FIGS. 1A, 1B, and 1C. As described herein, system 4000 may include one or more client computing devices 4010, a network 4020, server computing device 4030, and repository 4040. Client computing device 4010 may be configured to communicate with server 4030 via network 4020. Server 4030 may receive various requests from client computing device 4010 and retrieve various information from repository 4040 to address the requests from client computing device 4010. In some examples, server 4030 may generate information, such as queries and lists of potential medical problems for client computing device 4010.

Server 4030 may include one or more computing devices connected to client computing device 4010 via network 4020. Server 4030 may perform the techniques described herein, and a user may interact with system 4000 via client computing device 4010. Network 4020 may include a proprietary or non-proprietary network for packet-based communication. In one example, network 4020 may include the Internet, in which case each of client computing device 4010 and server 4030 may include communication interfaces for communicating data according to transmission control protocol/internet protocol (TCP/IP), user datagram protocol (UDP), or the like. More generally, however, network 4020 may include any type of communication network, and may support wired communication, wireless communication, fiber optic communication, satellite communication, or any type of techniques for transferring data between two or more computing devices (e.g., server 4030 and client computing device 4010).

Figure 1E:
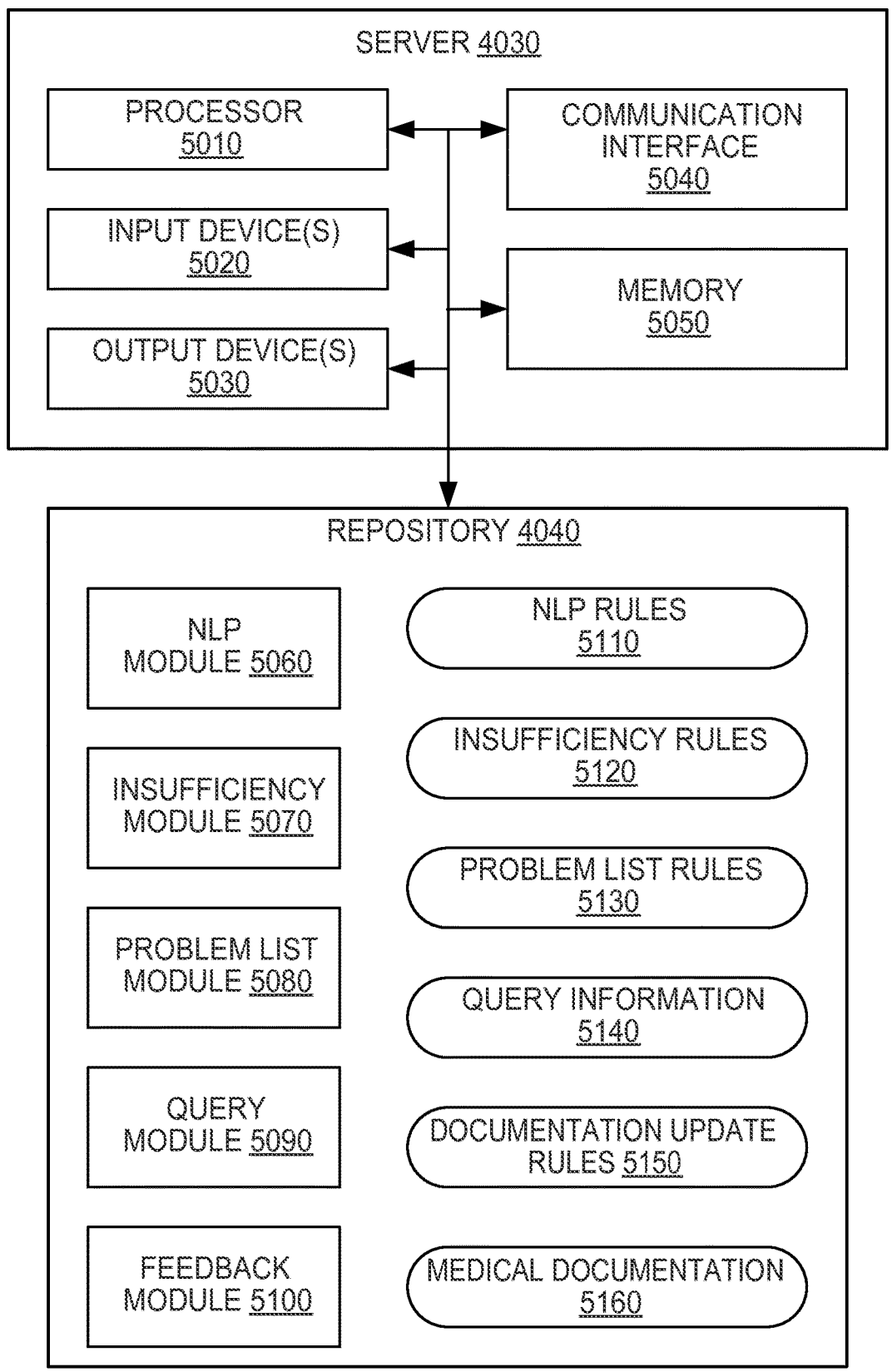
FIG. 1E is a block diagram illustrating the server and repository of the example of FIG. 1D.

Server 4030 may include one or more processors, storage devices, input and output devices, and communication interfaces as described in FIG. 1E. Server 4030 may be configured to provide a service to one or more clients, such as determining discrepancies within medical information (e.g., between different types of medical information), generating and outputting queries that identify discrepancies to the physician, and resolve the discrepancies based on additional user input. Server 4030 may operate on within a local network or be hosted in a Cloud computing environment. Client computing device 4010 may be a computing device associated with an entity (e.g., a hospital, clinic, university, or other healthcare organization) that provides information to a physician during a patient encounter and/or receives input documenting aspects of the patient encounter or addressing a query of list of potential medical problems. Examples of client computing device 4010 include personal computing devices, computers, servers, mobile devices, smart phones, tablet computing devices, etc. Medical documentation and responses to generated queries may be used to populate an EHR, track patient history, and/or generate billing for healthcare services. Client computing device 4010 may be configured to upload medical documentation to server 4030 for analysis, determination of any undocumented items, and generation of one or more queries soliciting user input addressing the undocumented items by server 4030. Alternatively, client computing device 4010 may be configured to retrieve queries, lists of potential medical problems, medical documentation, and/or other information generated by server 4030 and stored in repository 4040. Server 4030 may also be configured to communicate with multiple client computing devices 4010 associated with the same entity and/or different entities.

When a physician sees a patient in either an outpatient clinic or during an office visit (e.g., a patient encounter), the physician typically performs an evaluation of the patient, the patient's medical history and/or the patient's current medical condition. The physician may also perform a medical procedure on the patient during the patient encounter or prescribe treatment related to the patient's medical condition. The physician may create medical documentation memorializing these aspects of patient care. In addition, prior medical documentation may have been stored from previous patient encounters or other associated events.

However, some of the medical documentation may not be as complete as possible or may include ambiguous information. These issues with the medical documentation may result in incomplete patient records, potentially reduce the quality of care, and/or result in inaccurate billing. In addition, the potential medical problems identified in the medical documentation may not be as up to date or complete as possible. As described herein, system 4000 may be configured to determine any missing or ambiguous information in the medical document and generate queries delivered to physicians that solicit user input addressing this missing or ambiguous information. In addition, system 4000 may automatically generate lists of potential medical problems for review by a clinician to prevent physicians from manually populating a problem list associated with the patient.

System 4000 may operate to determine any missing or ambiguous information from medical documentation associated with the patient. In one example, server 4030 may be configured to receive documentation that includes a plurality of documented items related to the patient. The documentation may be received from repository 4040 or client computing device 4010. Server 4030 may also determine, based on at least a subset of the plurality of documented items in the documentation, one or more undocumented items missing from the documentation. The subset of the plurality of documented items and at least one of the one or more undocumented items define a medical concept, such as a diagnosis, treatment, or any other aspect related to the patient. Server 4030 may determine undocumented items from a comparison between documented items and possible medical documents, differences possibly being identified as possible undocumented items. Server 4030 may then generate, based on the one or more undocumented items, a code representative of the one or more undocumented items and output the code for use in generating a query. In some examples, server 4030 may generate multiple codes based on the undocumented items.

Server 4030 may be configured to solicit user input addressing the one or more undocumented items. For example, server 4030 may be configured to receive the code representative of the one or more undocumented items determined from the plurality of documented items related to the patient. The code may correspond with one or more possible clarifications or potential new items associated with other documented items previously identified. Based on the received code, server 4030 may generate one or more queries that each solicit user input addressing the one or more undocumented items and output the query, for display. The query may identify possible missing or ambiguous information and request clarification. The query may also include a list of selectable items that, when selected, address the query and/or a link to a response document. The physician may add or modify information in the response document to address the query.

Once server 4030 outputs the query for display, such as outputting the query for display via client computing device

4010, Client computing device 4010 may include input and/or output devices configured to display the query via a user interface. Client computing device 4010 may thus receive user input directed to the displayed query. Client computing device 4010 may then transmit, via network 4020, an indication of the user input to server 4030. Server 4030 may thus receive user input (or an indication of the user input) responsive to the query presented via the user interface, such that the user input addresses one or more undocumented items related to the query. Responsive to receiving the user input, server 4030 may be configured to generate updated information indicative of the user input and related to the patient. The updated information may clarify the missing or ambiguous information presented via the query. Server 4030 may then generate indicia indicative of the user input and output the indicia for display. In some examples, server 4030 may update the medical documentation of the patient with the updated information generated from the answer to the query.

In addition, server 4030 may be configured to manage medical information, such as automatically generating a list of potential medical problems from patient information. For example, server 4030 may identify one or more potential medical problems with the patient from encounter-related information associated with the patient. The encounter-related information may be received from client computing device 4010 and/or repository 4040. Server 4030 may generate a list comprising the one or more potential medical problems and output, for display, the list. Server 4030 may also be configured to receive an indication of selection input from a user, the selection input being associated with at least one of the potential medical problems, (e.g., via client computing device 4010) and update the list of potential medical problems according to the indication of the selection input. In this manner, server 4030 may automatically suggest medical problems for the patient and update or confirm the list of problems in response to receiving user input addressing the proposed list of potential medical problems. Server 4030 may repeat this process upon receiving new or updated encounter-related information. This server-performed process may relieve the physician from manual discovery and update of patient problems.

The processes described with respect to FIG. 1D and herein may be performed by one or more servers 4030. In other examples, client computing device 4010 may perform one or more of the steps attributed to server 4030, such as determining undocumented items and/or generation of queries. In this manner, system 4000 may be referred to a distributed system in some examples. Server 4030 may utilize additional processing resources by transmitting some or all of the medical information to additional computing devices.

Client computing device 4010 may be used by a user (e.g., a medical professional such as physician or assistant to a physician) to upload or select medical documents (e.g., encounter-related information), address queries, or provide input related to potential medical problems. Client computing device 4010 may include one or more processors, memories, input and output devices, communication interfaces for interfacing with network 4020, and any other components that may facilitate the processes described herein. In some examples, client computing device 4010 may be similar to computing device 4100 of FIG. 1F. In this manner, client computing device 4100 may be configured to perform one or more processes attributed to server 4030, such as determination of undocumented items or generation of queries, with the aid of server 4030 in some examples.

FIG. 1E is a block diagram illustrating server 4030 and repository 4040 of the example of FIG. 1D. As shown in FIG. 1E, server 4030 includes processor 5010, one or more input devices 5020, one or more output devices 5030, communication interface 5040, and memory 5050. Server 4030 may be a computing device configured to perform various tasks and interface with other devices, such as repository 4040 and client computing devices (e.g., client computing device 4010 of FIG. 1D). Although repository 4040 is shown external to server 4030, server 4030 may include repository 4040 within a server housing in other examples. Server 4030 may also include other components and modules related to the processes described herein and/or other processes. The illustrated components are shown as one example, but other examples may be consistent with various aspects described herein.

Processor 5010 may include one or more general-purpose microprocessors, specially designed processors, application specific integrated circuits (ASIC), field programmable gate arrays (FPGA), a collection of discrete logic, and/or any type of processing device capable of executing the techniques described herein. In some examples, processor 5010 or any other processors herein may be described as a computing device. In one example, memory 5050 may be configured to store program instructions (e.g., software instructions) that are executed by processor 5010 to carry out the techniques described herein. Processor 5010 may also be configured to execute instructions stored by repository 4040. Both memory 5050 and repository 4040 may be one or more storage devices. In other examples, the techniques described herein may be executed by specifically programmed circuitry of processor 5010. Processor 5010 may thus be configured to execute the techniques described herein. Processor 5010, or any other processes herein, may include one or more processors.

Memory 5050 may be configured to store information within server 4030 during operation. Memory 5050 may comprise a computer-readable storage medium or computer-readable storage device. In some examples, memory 5050 is a temporary memory, meaning that a primary purpose of memory 5050 is not long-term storage. Memory 5050, in some examples, may comprise as a volatile memory, meaning that memory 5050 does not maintain stored contents when the computer is turned off. Examples of volatile memories include random access memories (RAM), dynamic random access memories (DRAM), static random access memories (SRAM), and other forms of volatile memories known in the art. In some examples, memory 5050 is used to store program instructions for execution by processor 5010. Memory 5050, in one example, is used by software or applications running on server 4030 (e.g., one or more of modules 5060, 5070, 5080, 5090, and 5100) to temporarily store information during program execution.

Input devices 5020 may include one or more devices configured to accept user input and transform the user input into one or more electronic signals indicative of the received input. For example, input devices 5020 may include one or more presence-sensitive devices (e.g., as part of a presence-sensitive screen), keypads, keyboards, pointing devices, joysticks, buttons, keys, motion detection sensors, cameras, microphones, or any other such devices. Input devices 5020 may allow the user to provide input via a user interface.

Output devices 5030 may include one or more devices configured to output information to a user or other device. For example, output device 5030 may include a display screen for presenting visual information to a user that may or may not be a part of a presence-sensitive display. In other examples, output device 5030 may include one or more different types of devices for presenting information to a user. Output devices 5030 may include any number of visual (e.g., display devices, lights, etc.), audible (e.g., one or more speakers), and/or tactile feedback devices. In some examples, output devices 5030 may represent both a display screen (e.g., a liquid crystal display or light emitting diode display) and a printer (e.g., a printing device or module for outputting instructions to a printing device). Processor 5010 may present a user interface via one or more of input devices 5020 and output devices 5030, whereas a user may create encounter-related information (e.g., medical documentation), provide input addressing one or more queries, and/or provide input regarding a list of potential medical problems via the user interface (e.g., various user interfaces described herein). In some examples, the user interface generated and provided by server 4030 may be displayed by a client computing device (e.g., client computing device 4010).

Server 4030 may utilize communication interface 5040 to communicate with external devices via one or more networks, such as network 4020 in FIG. 1D, or other storage devices such as additional repositories over a network or direct connection. Communication interface 5040 may be a network interface card, such as an Ethernet card, an optical transceiver, a radio frequency transceiver, or any other type of device that can send and receive information. Other examples of such communication interfaces may include Bluetooth, 3G, 4G, and WiFi radios in mobile computing devices as well as USB. In some examples, server 4030 utilizes communication interface 5040 to wirelessly communicate with external devices (e.g., client computing device 4010) such as a mobile computing device, mobile phone, workstation, server, or other networked computing device. As described herein, communication interface 5040 may be configured to receive medical documents, codes, and/or transmit suggested codes and/or queries over network 4020 as instructed by processor 5010.

Repository 4040 may include one or more memories, repositories, databases, hard disks or other permanent storage, or any other data storage devices. Repository 4040 may be included in, or described as, cloud storage. In other words, information stored on repository 4040 and/or instructions that execute the techniques described herein may be stored in one or more locations in the cloud (e.g., one or more repositories 4040). Server 4030 may access the cloud and retrieve or transmit data as requested by an authorized user, such as client computing device 4010. In some examples, repository 4040 may include Relational Database Management System (RDBMS) software. In one example, repository 4040 may be a relational database and accessed using a Structured Query Language (SQL) interface that is well known in the art. Repository 4040 may alternatively be stored on a separate networked computing device and accessed by server 4030 through a network interface or system bus, as shown in the example of FIG. 1E. Repository 4040 may in other examples be an Object Database Management System (ODBMS), Online Analytical Processing (OLAP) database or other suitable data management system.

Repository 4040 may store instructions and/or modules that may be used to perform the techniques described herein related to determining missing or ambiguous items (e.g., undocumented items), generating queries, generating updated information based on input responsive to queries, and problem list generation. As shown in the example of FIG. 1E, repository 4040 includes NLP module 5060, insufficiency module 5070, problem list module 5080, query module 5090, and feedback module 5100. Processor 5010 may execute each of modules 5060, 5070, 5080, 5090, and 5100 as needed to perform various tasks. Repository 4040 may also include additional data such as information related to the function of each module and server 4030. For example, repository 4040 may include NLP rules 5110, insufficiency rules 5120, problem list rules 5130, query information 5140, documentation update rules 5150, and medical documentation 5160. Repository 4040 may also include additional data related to the processes described herein. In other examples, memory 5050 or a different storage device of server 4030 may store one or more of the modules or information stored in repository 4040.

Medical documentation 5160 may include all or a portion of the electronic health record (EHR) of one or more patients. Medical documentation 5160 may include encounter-related information, medical codes, or any other information related to the examination, diagnosis, and treatment of one or more patients. Server 4030 may retrieve at least a portion, or all, of medical documentation 5160 stored in repository 4040. Alternatively, server 4030 may receive medical documentation from another computing device via communication interface 5040 for analysis, and server 4030 may or may not store the received medical documentation as a part of medical documentation 5160 within repository 4040. In this manner, server 4030 may retroactively analyze medical documentation 5160 and/or analyze medical documentation as it is received from a physician. Medical documentation 5160 may include medical information for a single patient or multiple patients. In some examples, medical information from different patients and/or healthcare entities may be physically separated into different memories of repository 4040. Repository 4040 may implement security features designed to maintain patient privacy with respect to any stored data associated with the patient.

As described herein, server 4030 may operate to determine any missing or ambiguous information from medical documentation associated with the patient. In one example, processor 5010 may be configured to receive documentation that includes a plurality of documented items related to the patient. Processor 5010 may execute NLP module 5060 to analyze at least a portion of medical documentation 5160 (or other medical documentation) to identify documented items (e.g., medical terms related to examination, diagnosis, procedures, treatments, etc.). For example, NLP module 5060 may be configured to analyze the natural language of text and extract the documented items. Processing of the natural language may include analysis of each word, groups of words, and context. NLP module 5060 may identify words, sentences, sections and tag words with identifier codes to create a coded document. In some examples, the identifier codes may be fed to insufficiency module 5070 to generate any insufficiency codes. NLP module 5060 may perform the analysis of medical documentation based on NLP rules 5110 stored in repository 4040. The medical documentation may be received from repository 4040 or client computing device 4010, as some examples.

Processor 5010 may also execute insufficiency module 5070 to determine, based on at least a subset of the plurality of documented items in the medical documentation, one or more undocumented items missing from the documentation. The subset of the plurality of documented items identified from the medical document and at least one of the one or more undocumented items may define a medical concept, such as a patient condition, a diagnosis of the patient, a medical procedure performed on the patient, a treatment, or any other aspect related to the patient. Insufficiency module 5070 may determine the undocumented items by comparing the subset of the plurality of documented items to one or more predetermined sets of items. Insufficiency rules 5120 may store the predetermined sets of items as items pertaining to respective medical concepts. Insufficiency module 5070 may then be configured to identify, based on the comparison, at least one of the one or more predetermined sets of items that comprises each documented item of the subset.

In particular, insufficiency module 5070 may select, for each of the identified at least one predetermined sets of items, at least one item not included in the subset of documented items as at least one of the one or more undocumented items. These identified predetermined sets may thus include one or more undocumented items that, if selected by the physician as should be included in the medical documentation, render the medical concept as appropriate for the patient. Based on the one or more undocumented items, insufficiency module 5070 may generate a code representative of the one or more undocumented items and output the code for use in generating a query. In other words, insufficiency module 5070 may generate a code usable by query module 5090. In some examples, insufficiency module 5070 may generate multiple codes based on the undocumented items.

In some examples, the medical concept may be one of a plurality of medical concepts and the one or more undocumented items may include a plurality of undocumented items. In some cases, each of the plurality of undocumented items may be associated with a different one of the plurality of medical concepts. The undocumented items may, if added to the medical documentation, clarify one or more aspects of the patient's medical record. For example, if selected by a physician, at least one of the one or more undocumented items may complete, when combined with the subset of the plurality of documented items, a specific medical concept representative of at least one aspect of the patient's medical record.

In other examples, the undocumented items may link two or more different medical concepts together such that the patient's record is more accurate and more detailed information can be later derived from the linked medical concepts. In this manner, at least one of the determined undocumented items may link one, two, or even more medical concepts to another medical concept. In this manner, each of the linked medical concepts may be at least partially defined by at least one of the identified documented items. In some examples, the one or more undocumented items may confirm a possible medical concept that includes at least one or more of the identified documented items. Before confirmation of the undocumented items, the medical concept previously indicated may have been unconfirmed by only the subset of the plurality of documented items. In this manner, the documented items may be used to address missing or otherwise ambiguous information in the medical documentation.

In some examples, insufficiency module 5070 (or another module executed by server 4030 may generate statistics on documentation practices of physicians, other medical professionals, or organizations that submit documents for one or more patients. For example, insufficiency module 5070 may generate a report of what items are undocumented, the frequency or number of times the items were undocumented, and/or a ranking of the most frequency undocumented items. Insufficiency module 5070 may also indicate the selections received by the physician to correct the insufficiency. In this manner, the statistics may be used by physicians to learn how to improve patient documentation. These statistics may be generated for individual physicians, groups of physicians, organizations, total users, or any user requested group of users.

As discussed in greater detail herein, processor 5010 may be configured to execute query module 5090 to, responsive to receiving the code representative of the one or more undocumented items, generate, based on the code and for display, a query presenting at least one of the one or more undocumented items for selection by a user (e.g., a physician). Although NLP module 5060 is described as identifying documented items from the medical documentation and insufficiency module 5070 is described as determining any undocumented items and generating the respective code, a single module (e.g., NLP module 5060 or insufficiency module 5070) may perform each of these steps in other examples. In other examples, insufficiency module 5070 may include NLP module 5060. In this manner, although different modules are described as performing respective processes herein, other examples may include a different number of modules (e.g., only a single module or many specialized modules) for performing each process. Insufficiency module 5070 may be similar to DICE 3050 of FIG. 1C.

Processor 5010 may also be configured to solicit user input addressing the one or more undocumented items. For example, processor 5010 may be configured to execute query module 5090 to receive the code representative of the one or more undocumented items determined from the plurality of documented items related to the patient (as described above with respect to insufficiency module 5070). The code may correspond with one or more possible clarifications or potential new items associated with other documented items previously identified. Based on the received code, query module 5090 may generate one or more queries that each solicit user input addressing the one or more undocumented items and output the query for display. The query may identify possible missing or ambiguous information and request clarification.

Processor 5010 may transmit the generated query to present, via a display device, a user interface comprising the query. For example, processor 5010 may output, via communication interface 5040 and a network (e.g., network 4020), generated queries to another computing device such as client computing device 4010 of FIG. 1D for display to the physician. Processor 5010 may also receive, via communication interface 5040, indications of the user input provided to address the queries.

Each query generated by query module 5090 according to the rules stored as query information 5140 can solicit different types of user input. For example, a query may include one or more selectable items (e.g., items within a list) that, when selected, addresses the one or more undocumented items identified in the query. In this manner, the selectable items may include a list of a plurality of different options. Each option may correspond to a respective undocumented item, a request to hold the query to address at another time, a request to discuss the query as not applicable, or any other such actions. Although user input may be limited to selection of a single selectable item, some queries may permit selection of multiple selectable items to address the query in some examples.

In one example, at least one of the one or more selectable items may correspond to a respective one of the one or more undocumented items and selection of one of the selectable items addresses the one or more undocumented items represented by the code from which the query was generated. In some examples, one of the one or more selectable items includes a rejection input that rejects all of the one or more selectable items corresponding to the respective one of the one or more undocumented items. In this manner the rejection input may indicate that none of the undocumented items are applicable to the patient. However, selection of the rejection input may still address the one or more undocumented items represented by the code and the query.

The query may include a question or a statement as part of the solicitation to the physician. A user interface presented by the client computing device (e.g., device 4010) may include the query. Although client computing device 4010 may generate the user interface, processor 5010 and/or a user interface module may be configured to generate the user interface and transmit the data to client computing device 4010. Client computing device 4010 may receive, via the user interface, a query response that is responsive to either the question or the statement. Client computing device 4010 may then transmit an indication of the query response to server 4030. In some examples, the query may include a list of selectable items that, when selected, address the query. In addition, or alternatively, the query may include a link to a response document within which the physician may add or modify information to address the query. In this manner, the response document may be configured to receive free form text from the physician. The physician may utilize the response document when none of the selectable items appropriately address the query and/or the physician desires to provide additional information.

In some examples, query module 5090 may generate a plurality of queries associated with one or more respective undocumented items. Query module 5090, or another module executed by processor 5010, may be configured to generate, for display in association with the patient, indicia representative of a number of the plurality of queries requiring a respective response. In other words, query module 5090 may generate one or more queries for a single patient and processor 5010 may present the indicia as an indication when there are one or more queries that need to be addressed. Such indicia may be presented as part of a notification or other alert indicating that queries remain unaddressed. In addition, processor 5010 may be configured to generate, based on at least a portion of encounter-related information associated with the patient, medical evidence associated with the patient. Processor 5010 may output, for display with one or more of the queries, at least a portion of the medical evidence. The medical evidence may be provided so that the physician can review the medical evidence when determining which selectable item should be selected for each query. The medical evidence may be provided as part of the same window of the query or within a separate portion of the user interface.

Processor 5010 may process responses to queries to update, based on a received query response to a presented query, documentation or other information associated with the patient to define one or more medical concepts. In this manner, processor 5010 may automatically address missing or ambiguous information represented by the query by updating medical documentation of the patient (such as at least a portion of the patient's EHR). Processor 5010 may also output additional information for display with (e.g., simultaneously on the same screen) the one or more queries. For example, processor 5010 may be configured to present, via a user interface, a query with a problem list associated with the patient, and wherein user input solicited by the query triggers an update to the problem list. The problem list may be a list of potential medical problems, a confirmed list of problems, or some combination therein. Upon receiving responses to queries, problem list module 5080 may update the list of potential medical problems to convey more up to date and accurate information regarding the patient.

Once processor 5010 outputs the query for display, such as outputting the query for display via client computing device 4010, client computing device 4010 may utilize input and/or output devices configured to display the query via a user interface. Client computing device 4010 may thus receive user input directed to the displayed query. Client computing device 4010 may then transmit, via network 4020, an indication of the user input to server 4030. Processor 5010 may then receive the user input (or an indication of the user input) responsive to the query that was presented via the user interface, such that the user input addresses one or more undocumented items related to the query. Responsive to receiving the user input, processor 5010 may execute feedback module 5100 to generate updated information indicative of the user input and related to the patient, according to the rules stored in documentation update rules 5150. The updated information may clarify the missing or ambiguous information presented via the query. Processor 5010 may also generate indicia indicative of the user input and output the indicia for display. In some examples, feedback module 5100 may update the medical documentation (e.g., medical documentation 5160) of the patient to include the updated information generated from the answer to the query. In some examples, feedback module 5100 is configured to generate the updated information indicative of the user input and related to the patient, and another module is configured to generate the indicia indicative of the user input. The other module may be a user interface module or other such module associated with managing various indicia.

In some examples, the indicia may include a textual representation indicative of the updated information that addresses the one or more undocumented items. For example, the indicia may comprise a visual indicia that identifies updated information from a query response. Since the updated information may be suggested based on a physician input to a query, the physician may prefer to confirm that the updated information is in fact accurate. Therefore, feedback module 5100 may be further configured to receive user input approving the textual representation. In some examples, the user input approving the textual representation may include an electronic signature from a user (e.g., the physician) that provided the user input responsive to the query. The textual representation may not be completely accurate in some examples. Therefore, feedback module 5100 may also be configured to receive modification user input in the form of one or more edits to the textual representation. Feedback module 5100, or another module executed by processor 5100, may be configured to modify, based on the edits to the textual representation, the updated information. In this manner, processor 5010 may be configured to only update medical documentation in response to receiving confirmation from the physician that the update is accurate. In response to receiving the user input approving the textual representation, feedback module 5100 may thus associate the updated information with the medical documentation.

As described herein, the medical documentation 5160 may include the plurality of documented items related to the patient. The user input addressing the one or more queries can clarify any issues with medical documentation 5160, such as adding one or more medical concepts not identified, or confirmed, without the user input. Therefore, feedback module 5100 may be configured to update, based on the user input responsive to the queries, the medical documentation 5160 associated with the patient to define one or more additional medical concepts. An additional medical concept may be a more specific medical concept than previously identified or new medical concepts for which the previous medical documentation did not adequately identify.

In some examples, medical documentation 5160 may include, or be defined as, the EHR for the patient. Therefore, processor 5010 may update the medical documentation directly. In other examples, medical documentation 5160 may be stored and/or managed by another server, computing device, or system. In this manner, processor 5010 may be configured to generate a request to update the medical documentation associated with the patient with the updated information and transmit, from server 4030, the request to another computing system that maintains the medical documentation 5160. The request may include the updated information or an indication of the updated information.

Processor 5010 may also be configured to manage medical information associated with a patient, such as automatically generating a list of potential medical problems from patient information. For example, processor 5010 may execute problem list module 5080 to identify one or more potential medical problems with the patient from encounter-related information associated with the patient. The encounter-related information may be received from client computing device 4010 and/or repository 4040, and medical documentation 5160 may include the encounter-related information in some examples. Problem list module 5080 may, based on the rules stored as problem list rules 5130, generate a list comprising the one or more potential medical problems and output, for display, the list. Problem list module 5080 may also be configured to receive an indication of selection input from a user and associated with at least one of the potential medical problems (e.g., via client computing device 4010) and update the list of potential medical problems according to the indication of the selection input and according to the problem list rules 5130. In this manner, problem list module 5080, and processor 5010, may automatically suggest medical problems for the patient and update or confirm the list of problems in response to receiving user input addressing the proposed list of potential medical problems. Problem list module 5080 may repeat this process upon receiving new or updated encounter-related information. This server-performed process may relieve the physician from manual discovery and update of patient problems.

In some examples, problem list module 5080 may analyze the encounter-related information directly to generate the potential medical problems. In other examples, NLP module 5060 may identify the one or more potential medical problems from the encounter-related information and problem list module 5080 may use the potential medical problems to generate the list of potential medical problems. Alternatively, processor 5010 may leverage NLP module 5060 to identify documented items or otherwise code the encounter-related information, and problem list module 5080 may determine the potential medical problems for the list based on the identified documented items.

Client computing device 4010 may include a display device configured to present the list of the one or more potential medical problems in a user interface and an input device configured to receive the selection input from the user and generate the indication of the selection input. Client computing device 4010 may transmit the indication of the selection input back to server 4030 for processing by processor 5010 and potentially updating the list of potential medical problems by problem list module 5080. Problem list module 5080 may update the list of potential medical problems in multiple ways. Based on the selection input, problem list module 5080 may update the list by at least one of reordering the problems in the list, modifying at least one of the problems in the list, removing at least one of the problems from the list, or adding one or more problems to the list. In this manner, updating the list may or may not involve updating one of the potential medical problems within the list.

Problem list module 5080 may be configured to generate a signal to update a problem list consistent with the received selection input. The problem list is different from the list of one or more potential problems, as the problem list is maintained as part of an electronic health record (EHR) associated with the patient. In other words, physician input used to modify the list of potential medical problems may be transferred to update a separate problem list maintained as a part of the permanent EHR for the patient. In this manner, processor 5010 may be configured to transmit, via communication interface 5040, the signal to a computing system configured to store the EHR associated with the patient. Alternatively, processor 5010 may be configured to directly update, according to the signal, the EHR associated with the patient in the situation where the EHR is under control of processor 5010 (e.g., the EHR is stored in repository 4040). The signal may, in some examples, include information consistent with an HL7 or a Clinical Document Architecture standard.

Problem list module 5080 may also output, for display, information associated with the list of potential medical problems. In one example, problem list module 5080 may, prior to outputting the list, output, for presentation via a display device, visual indicia indicative of the one or more potential medical problems having been identified. The visual indicia may be representative of new potential medical problems that have been identified by problem list module 5080 from encounter-related information. In some examples, the visual indicia may indicate that the potential medical problem has not yet been confirmed by physician input. The visual indicia may be modified, or changed to different indicia, once a potential medical problem within the list has been confirmed by the physician input.

In this manner, problem list module 5080 may be configured to receive an indication of edit input from the user that edits one of the one or more potential medical problems. In response to receiving the edit input, problem list module 5080 may update the one of the one or more potential medical problems according to the edit input. In some examples, the edit input may include a request to eliminate the one of the one or more potential medical problems from the list. Instead of, or in addition to an edit input, problem list module 5080 may be configured to receive validation-related user input from the user for the list of potential medical problems. The validation-related user input may indicate user acceptance of the one or more potential medical problems of the list as being representative of current medical problems associated with the patient. The validation-related user input may be provided separately for each of the potential medical problems or as a global validation-related user input accepting the entre list of potential medical problems. Problem list module 5080 may also generate a response document consistent with the selection input, the response document memorializing the validation of the at least one of the potential medical problems. The response document may include the accepted potential medical problems, any changes to the potential medical problems, or any other information related to the selection input received for the list of potential medical problems.

Although server 4030 is described as configured to perform the natural language processing of the medical documents, determine undocumented items, and generate queries, generate updated information, and suggest potential medical problems, each of these processes may be performed by different computing devices in other examples. For example, server 4030 may not be configured to determine the undocumented items missing from documentation. Instead, server 4030 may be configured to receive the undocumented items, or code representing such missing or ambiguous information, from another computing device and generate the corresponding queries. In this manner, different devices or systems may be configured to handle the tasks of analyzing medical documents, determine discrepancies in medical information and/or generate queries.

Figure 1F:
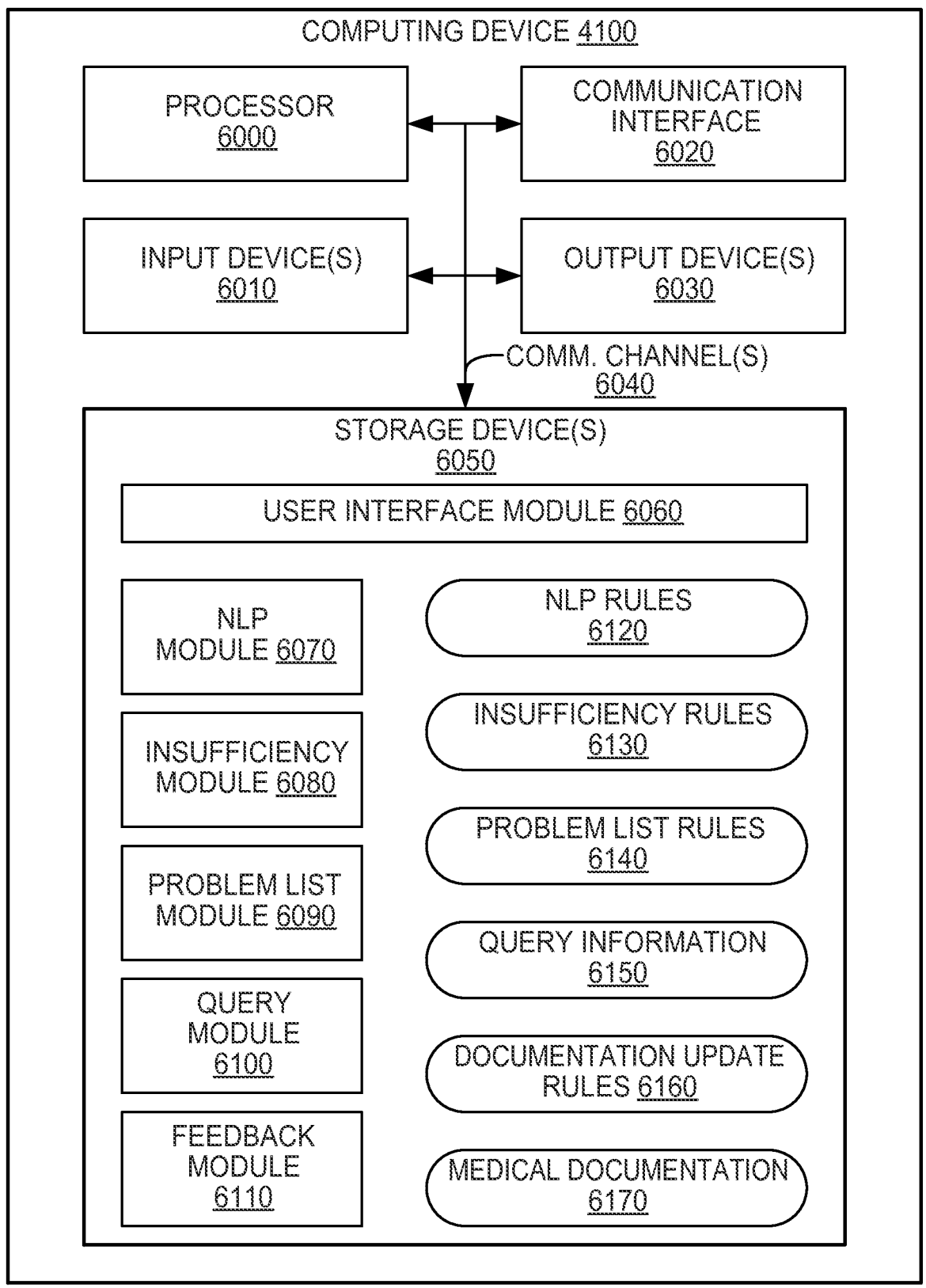
FIG. 1F is a block diagram illustrating a stand-alone computing device configured to analyze and/or manage medical documentation consistent with this disclosure.

FIG. 1F is a block diagram illustrating a stand-alone computing device 4100 configured to analyze and/or manage medical documentation consistent with this disclosure. Computing device 4100 may be substantially similar to server 4030 and repository 4040 of FIG. 1E. However, computing device 4100 may be a stand-alone computing device configured to perform the analysis of medical information and generation of queries. Computing device 4100 may be configured as a workstation, desktop computing device, notebook computer, tablet computer, mobile computing device, or any other suitable computing device or collection of computing devices.

As shown in FIG. 1F, computing device 4100 may include processor 6000, one or more input devices 6010, one or more output devices 6030, communication interface 6020, and one or more storage devices 6050, similar to the components of server computing device 4030 of FIG. 1E. In some examples, computing device 4100 may be similar to client computing device 4010 of FIG. 1D. Computing device 4100 may also include communication channels 6040 (e.g., a system bus) that allows data flow between two or more components of computing device 4100, such as between processor 6000 and storage devices 6050. Computing device 4100 also includes one or more storage devices 6050, such as a memory, that stores information such as instructions for performing the processes described herein and data such as medical documentation for a patient and algorithms for identifying missing information and/or generating associated queries.

Storage devices 6050 may include data for one or more modules and information related to the determination of undocumented items, the generation of queries, and the generation of updated information from responses to the queries described herein. For example, storage devices 6050 may include NLP module 6070, insufficiency module 6080, problem list module 6090, query module 6100, and feedback module 6110, similar to the modules described with respect to repository 4040 of FIG. 1E. Storage devices 6050 may also include information such as NLP rules 6120, insufficiency rules 6130, problem list rules 6140, query information 6150, documentation update rules 6160, and medical documentation 6170, similar to the information described as stored in repository 4040.

The information and modules of storage devices 6050 of computing device 4100 may be specific to a healthcare entity that employs computing device 4100 to identify insufficiencies in medical documentation and address such insufficiencies in the medical information generated by healthcare professionals (e.g., physicians and/or nurses) associated with the healthcare entity. For example, insufficiency rules 6130 may contain a specific codeset that is used by the healthcare entity to identify medical concepts. In any case, computing device 4100 may be configured to perform any of the processes and tasks described herein and with respect to server 4030 and repository 4040. Storage devices 6050 may also include user interface module 6060, which may provide a user interface for a user via input devices 6010 and output devices 6030.

In some examples, input devices 6010 may include one or more scanners or other devices configured to convert paper medical documents into electronic medical documents that can be analyzed by computing device 4100. In other examples, communication interface 6020 may receive electronic medical documents from a repository or individual clinician device on which the medical documents are initially generated. Communication interface 6020 may thus send and receive information via a private or public network.

FIGS. 2-22 includes screenshots of a user interface, e.g., from user interface module 1060, that presents patient information and queries generated by a query generation module (e.g., modules 1040 or 5090). These screenshots may be generated by a processor for display to a user based on the techniques described herein. The queries are either computer generated (CAPD) or specialist generated (specialist queries), or are problem-list related (e.g., queries related to a list of potential medical problems). The queries are generally directed to a physician who is a user of a CDI query system, such as the system of FIG. 1A or system 4000 of FIG. 1D.

Figure 2:
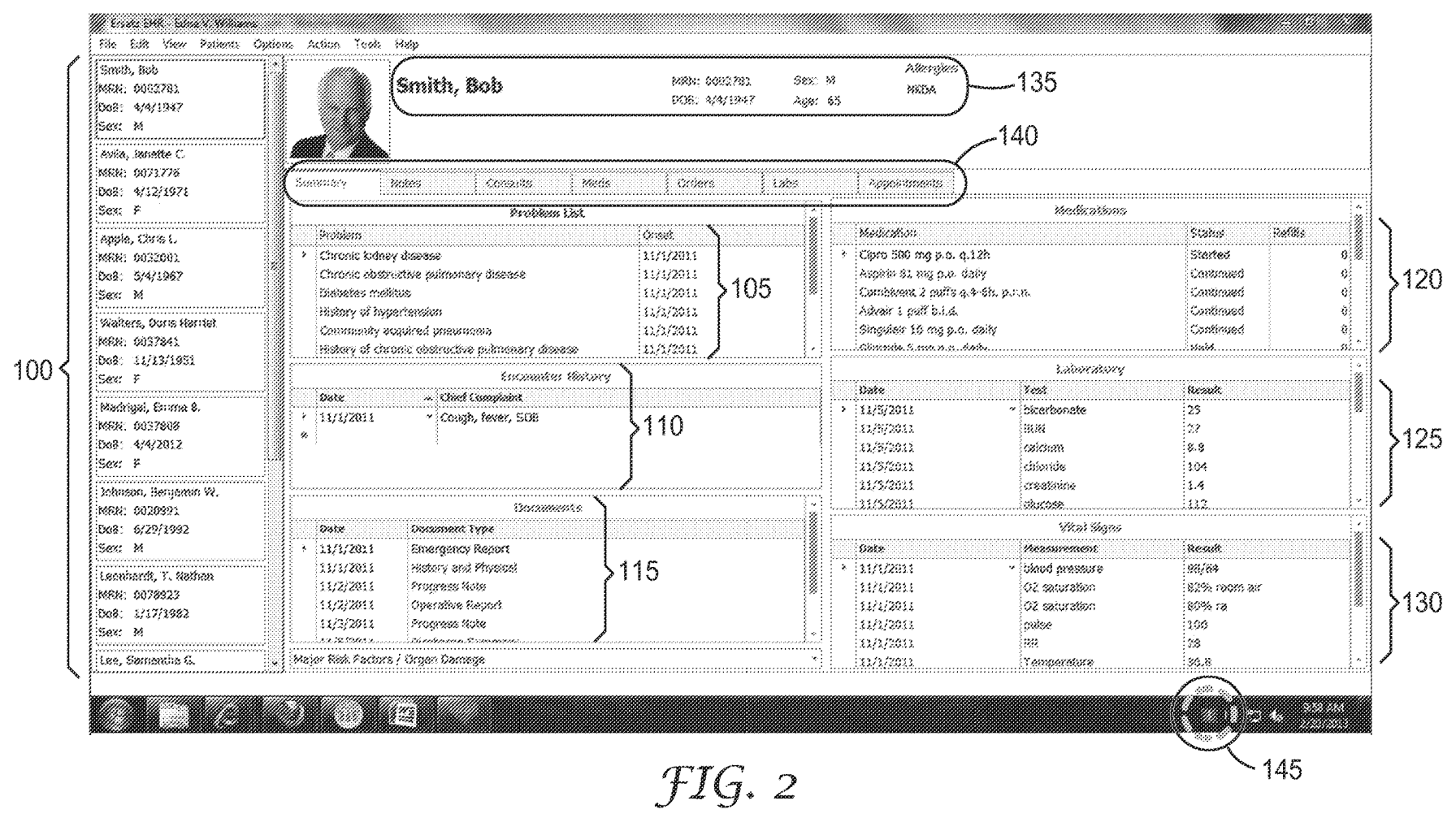

FIG. 2 shows an example mock EHR for example patient Bob Smith. In practice, many hospitals and healthcare providers will have their own EHR systems, and FIG. 2 is merely an example generic system. Various EHRs are shown in column 100, each associated with a respective single patient. The first EHR, for Bob Smith, has been selected and thus information related to Bob Smith is shown in the remaining portion of the screen. At this point, CDI query system idles, awaiting a signal indicative of a physician logging onto the system (indicia 145 shows that CDI query system is active). The CDI query system may be accessible via indicia 145, with or without a login event.

As shown in FIG. 2, the EHR may include different fields with different information. Problem list 105 may include problems in the problem list maintained within the EHR. Encounter history 110 may include a list of the patient encounters. Document field 115 may include a list of the documents stored as part of the HER, which may or may not be available for viewing by the physician. Patient information 135 may include patient data describing the patient, and navigation bar 140 may include different portions of the EHR accessible to the physician, such as a Summary, Notes, Consults, Meds, Orders, Labs, and Appointments. Medication field 120 may include a list of the medications prescribed to the patient and any relevant information associated with each medication. Laboratory field 125 may list the tests performed on the patient and any applicable results. Vital sign field 130 may include a list of various vital signs taken for the patient with the date and result also listed for reference. More or fewer fields may be provided in other views of the EHR.

Once a physician logs on to the system, the CDI query system may pull the physician's profile and determine what, if any, queries are outstanding for the physician. An indication of the outstanding queries is shown in dialog box 200, in FIG. 3. For example, dialog box 200 states that "4 patients with clarification requests" and indicates that the user can click on dialog box 200 to view the queries. Dialog box 200 may be similar to a notification or alert for the user.

FIG. 4 shows an example user interface with panel 210 generated by interface of the CDI query system. FIGS. 4-9, 11-18, and 20 described herein refer to panel 210, but each instance of panel 210 may include different output or information as the panel may change as the user interacts with the system. As can be seen, panel 210 is overlaid upon the EHR user interface and may run independently of whatever EHR system that exists (e.g., panel 210 may be a second window or a pop-up window). In the case shown in FIG. 4, panel 210 shows that Dr. Williams (hereinafter, user) has logged into the system. User's patients are shown in the patient summary area 220 of panel 210. Visual indicia 230 may be associated with each of the patients for which there is an outstanding query. In addition, visual indicia 230 may indicate the number of queries outstanding for that particular patient. In some examples, the system may order (or prioritize) the patients based on the number of outstanding queries (e.g., patients with more queries may be placed higher in the list of patients in patient summary area 220. Message dialog 235 shows whether there are any messages for the doctor. Messages may include questions, updates or alerts about a patient sent from one physician to another or sent from a CDI specialist or coder to the physician. Messages can also include questions or additional information about a specific query that a physician may send to a CDI specialist, and vice versa.

Figure 5:
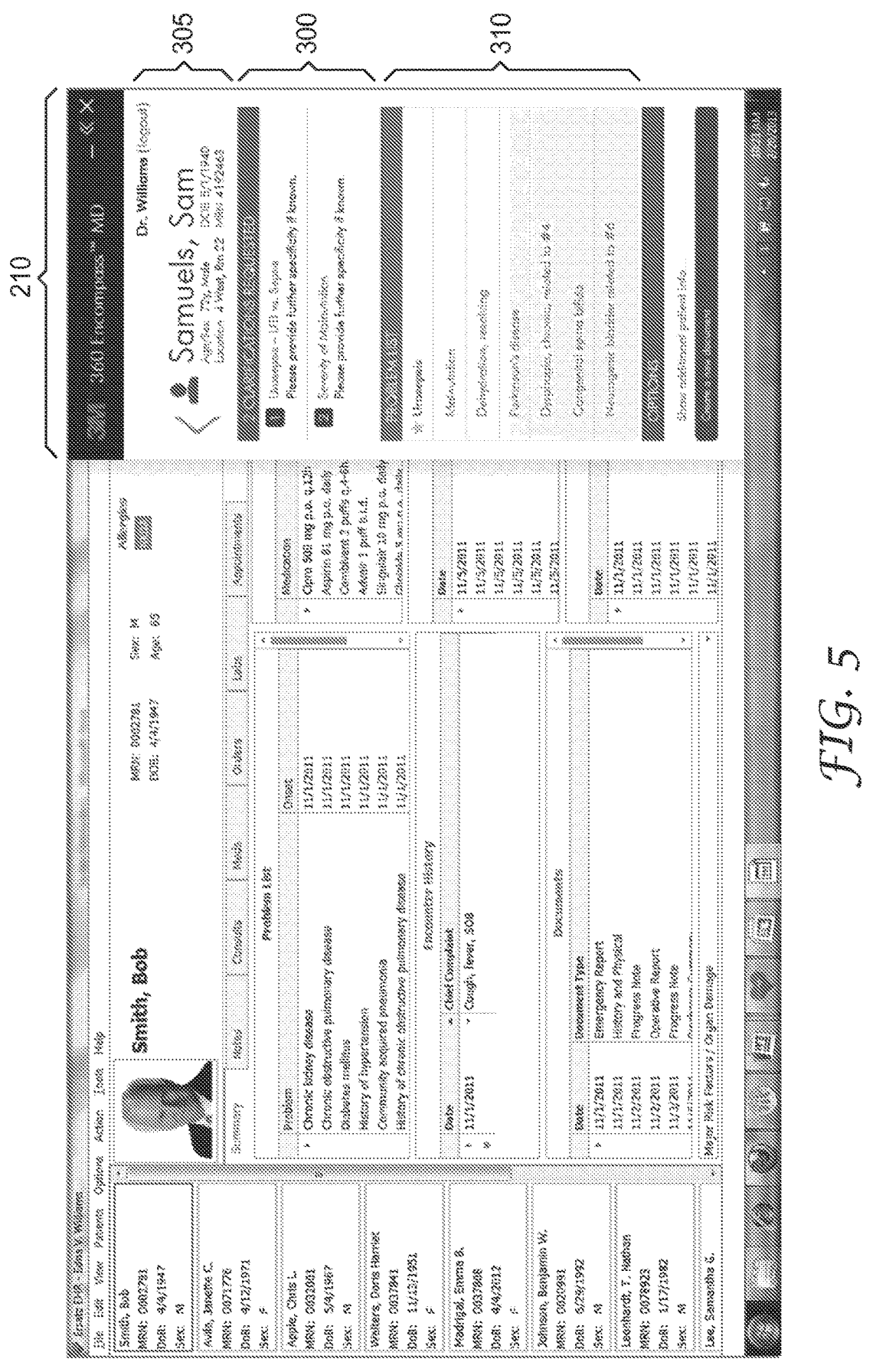

FIG. 5 illustrates an example user interface showing example queries. When the user selects the second listed patient, Sam Samuels, the CDI query system presents the interface shown in FIG. 5 that includes a modified panel 210. Panel 210 may include patient data 305, outstanding query summaries 300 (example queries), and list 310 of potential medical problems (e.g., a problem list that includes at least one suggested problems). Each of the queries are solicitations for clarification regarding medical documentation. As mentioned above, the list of potential medical problems contains a code-consistent (either SNOMED CT or ICD-9 or ICD-10) list of the most important and relevant information for the patient's current hospital visit (current problem list) and may also show a historical summary of the patient's past medical record (historical problem list—not shown in FIG. 5). The physician can view, edit, update, add-to and validate one or more problems of list 310, and can access the historical problem list for additional information about the patient. Suggested problems (those identified by the NLP engine, but not yet validated) are also presented to the physician, as will be described in further detail later.

FIG. 6 illustrates details about a selected query. When the user selects the first outstanding query in query summary 300 (that is, the one related to urosepsis), the CDI query system presents the interface shown in FIG. 6 via panel 210. Panel 210 includes the query asking for clarification of this diagnosis as well as a query pick list 350 that shows available options (e.g., a list of selectable items) for responding to this query. The query itself and the options for responding may be generated by the query generation module. Other options 360 are available to the physician to show the physician more key information associated with this patient and associated with the query to enable the physician to appropriately and accurately answer the query. One of the options 360 may include viewing of the document that contains the specific evidence that triggered this query ("show evidence"). If the physician were to select this link, the system may display the source documents that supported the query, with specific words, terms, or other key evidence that led to generation of this query being highlighted so that physician can quickly reference the information that triggered this query. This evidence may allow the physician to respond quicker and more accurately to the query than if the physician would need to dig into the EHR to determine how to answer the query.

Figure 7:
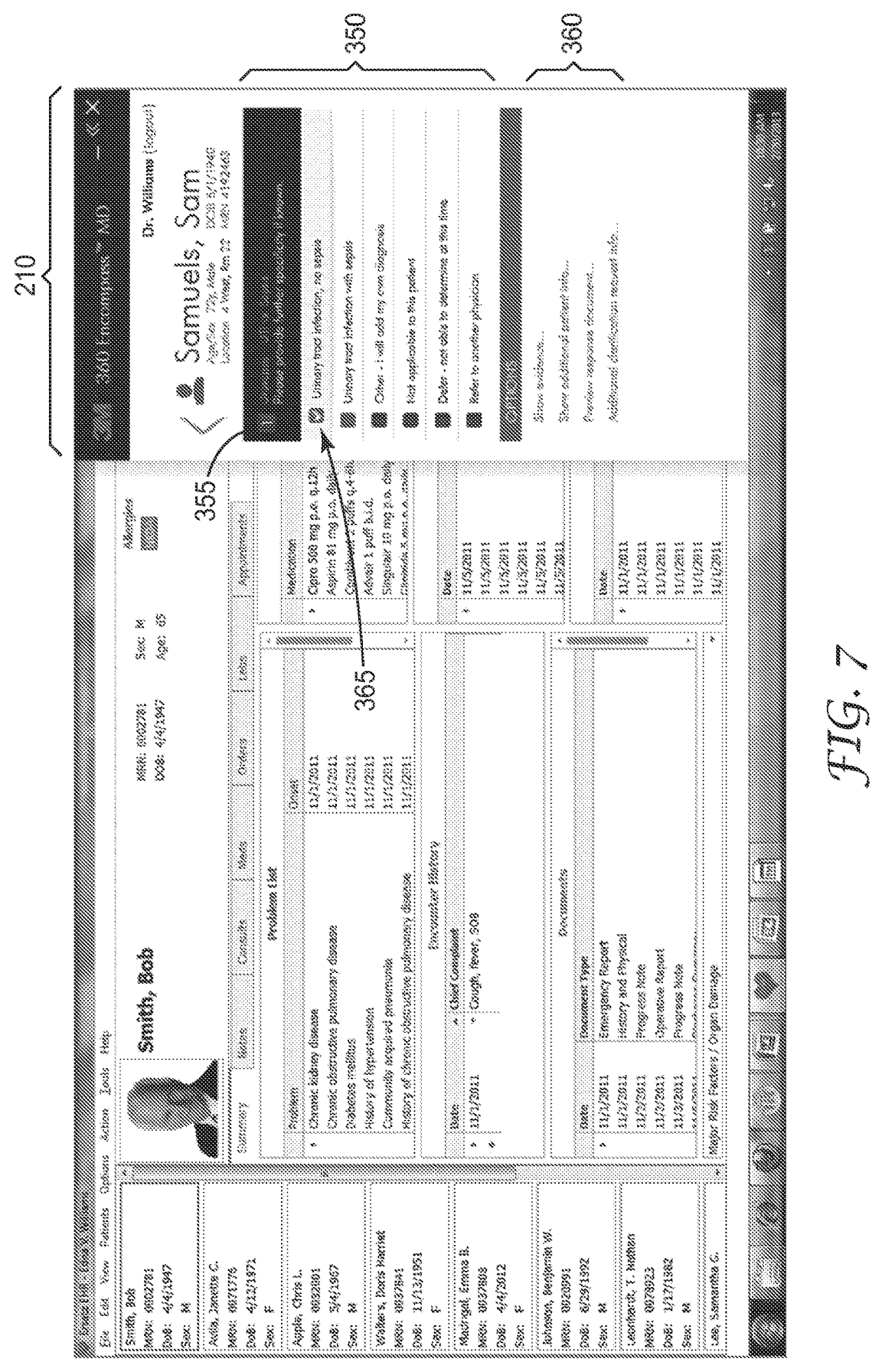

The response choices displayed in pick list 350 are, in some examples, pre-set options that have been scripted by one or more documentation improvement experts to be complete and compliant with current industry rules and regulations regarding querying physicians. The specific query associated with pick list 350 may be "Urosepsis—UTI vs. Sepsis" and "Please provide further specificity if known." Various selectable options are shown in pick list 350, in the form of a pick list that the user may select from. As shown in the example of FIG. 7, the user has selected selects the first pick list option 365, "Urinary tract infection, no sepsis" for query 355 related to urosepsis. Although only one item or option may typically be selected from pick list 350, multiple items may be selected in certain situations to clarify the query.

FIG. 8 shows the second clarification query 366 of the outstanding query summaries 300 relevant to the patient (see FIG. 5). The clarification query may include detailed information, such as "Severity of Malnutrition" and "Please provide further specificity if known." Query 366 solicits user input to select one item from pick list 350 associated with the query 366, and user input is shown as selecting "Moderate malnutrition". Upon receiving the selection of one of the selectable items in pick list 350, the system may generate update information related to the query.

Figure 9:
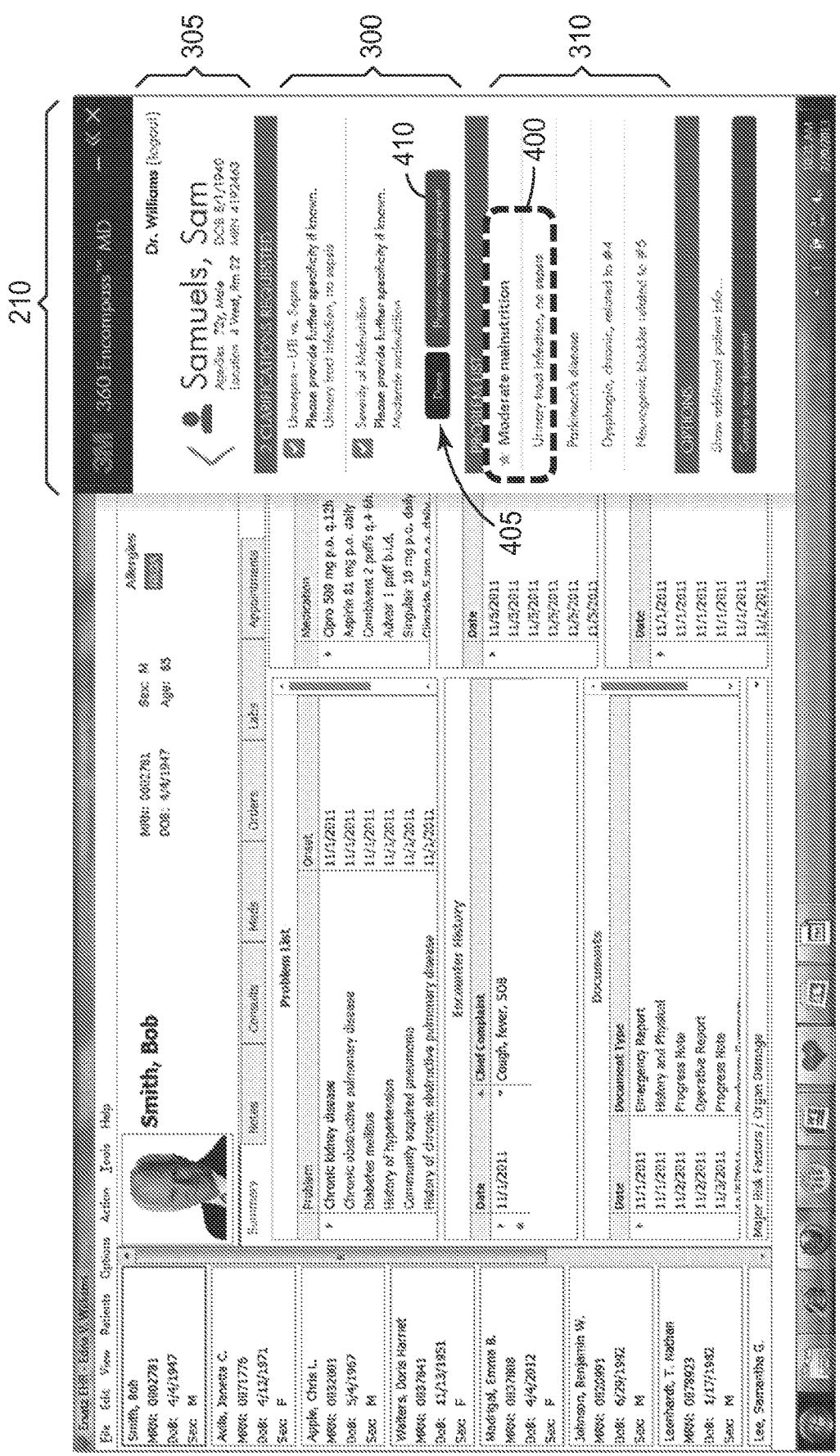
FIG. 9 is an illustration of an example user interface that presents addressed queries and an updated list of potential medical problems.

FIG. 9 shows the now updated panel 210, reflecting a user interface state in which both of the outstanding clarification queries 300 have been addressed by the user (signified by check marks next to each query). User's responses to clarification queries 300 have resulted in the NLP engine suggesting new problems 400 that are listed in updated list 310 of potential medical problems, showing the patient's principal problem as "moderate malnutrition." Newly suggested problems, i.e. ones that are not yet associated with a patient's problem list, may be associated with particular visual indicia (not shown in FIG. 9). For example, new potential medical problems added to the list may be highlighted in a certain way to signify they are being suggested to the physician but have not yet been validated by the physician. Also, there may be an alert that is shown to the physician in the clarification query 300 area, or elsewhere, indicative of the new status of the potential medical problem.

The principal problem of the patient may be associated with visual indicia in the form of a star, as shown in the top problem of new problems 400. Clicking in the problem list area may make the problem list editable (see FIG. 11), allowing the user physician to re-order, modify, add, or eliminate problems from the list 310. Once the user is satisfied with the problems of list 310, the user may provide input requesting that the problem list be saved. Upon saving the problem list, the system may automatically generate a response document as the official record of the response to the queries. The response document may be inspected and/or modified by the user, by selecting indicia 410 which indicates "preview response document." This response document is shown in the example of FIG. 10.

Returning now to FIG. 9, user may signify to the CDI query system that the user is done by selecting done indicia 405. Selecting done indicia 405 in this instance would result in closing panel 210 of the CDI query system with respect to this patient and sending the signed (e.g., validated), new document to the EHR without any further physician actions or intervention. In this manner, panel 210 and the queries can allow the physician to address issues with medical documentation without manually entering the EHR for the patient.

Figure 10:
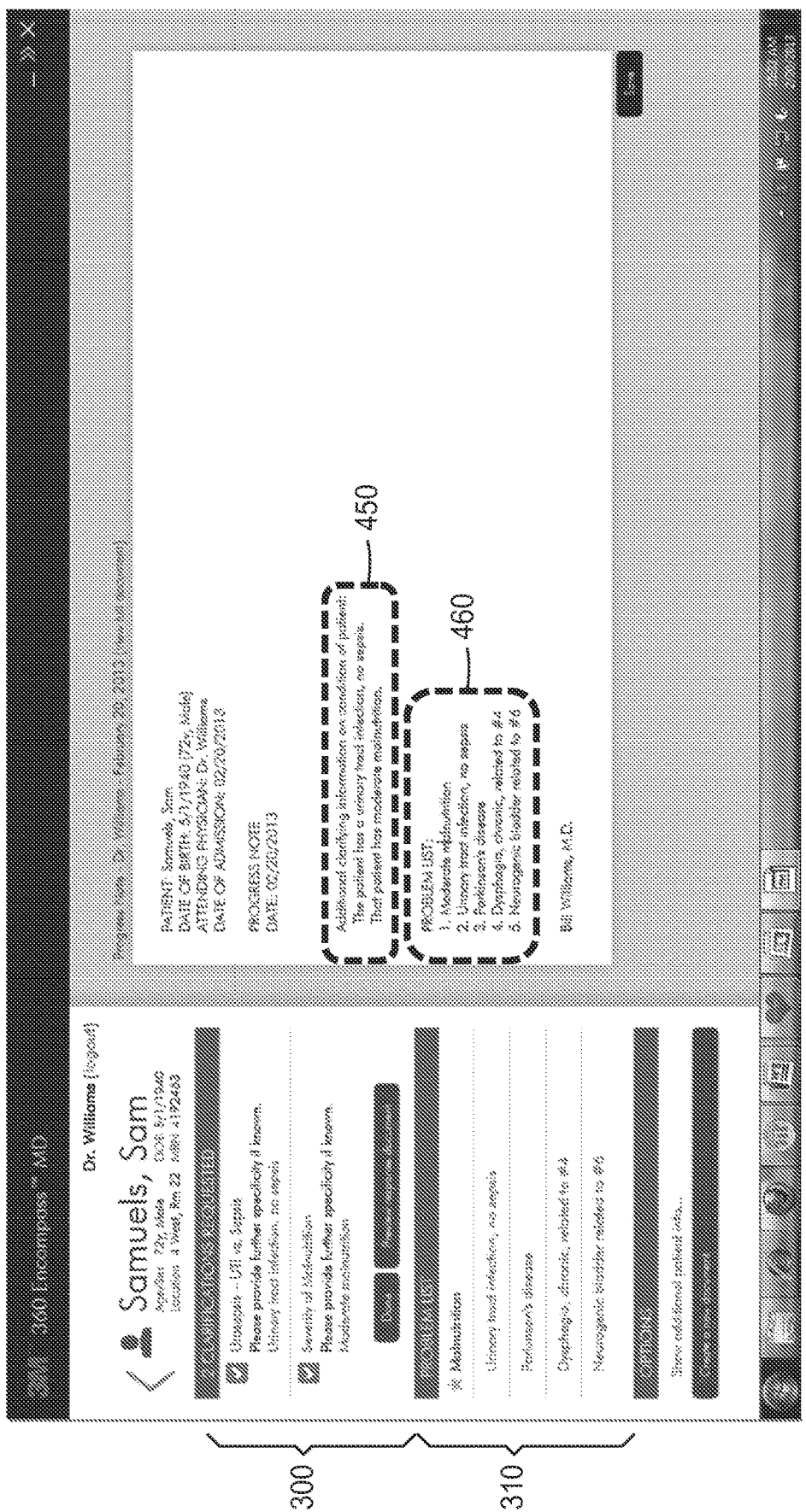
FIG. 10 is an illustration of an example user interface that includes a response document representing a response to a query.

FIG. 10 shows an example response document that has been automatically generated as a result of the user's response to the clarification queries 300. The system has shifted panel 210 to the left of the screen to make room for presentation of the automatically generated document in the right pane of the user interface. Included in the response document are text sections associated with each query. Text section 450 is associated with the first clarification query having to do with urosepsis, and text section 460 is associated with the second clarification query having to do with the list of potential medical problems. The entire response document may be editable by the user. The user may edit the document as desired, the system may receive such user input, and the user may then click "save" to electronically sign the document. Saving the document may cause the system to return the user to main CDI query system interface shown in FIG. 9. Within the interface of FIG. 9, the user may at this point desire to update the list of potential medical problems, particularly the order of the list. The user may click anywhere within the list of problems to be brought to the user interface shown in FIG. 11.

Figure 11:
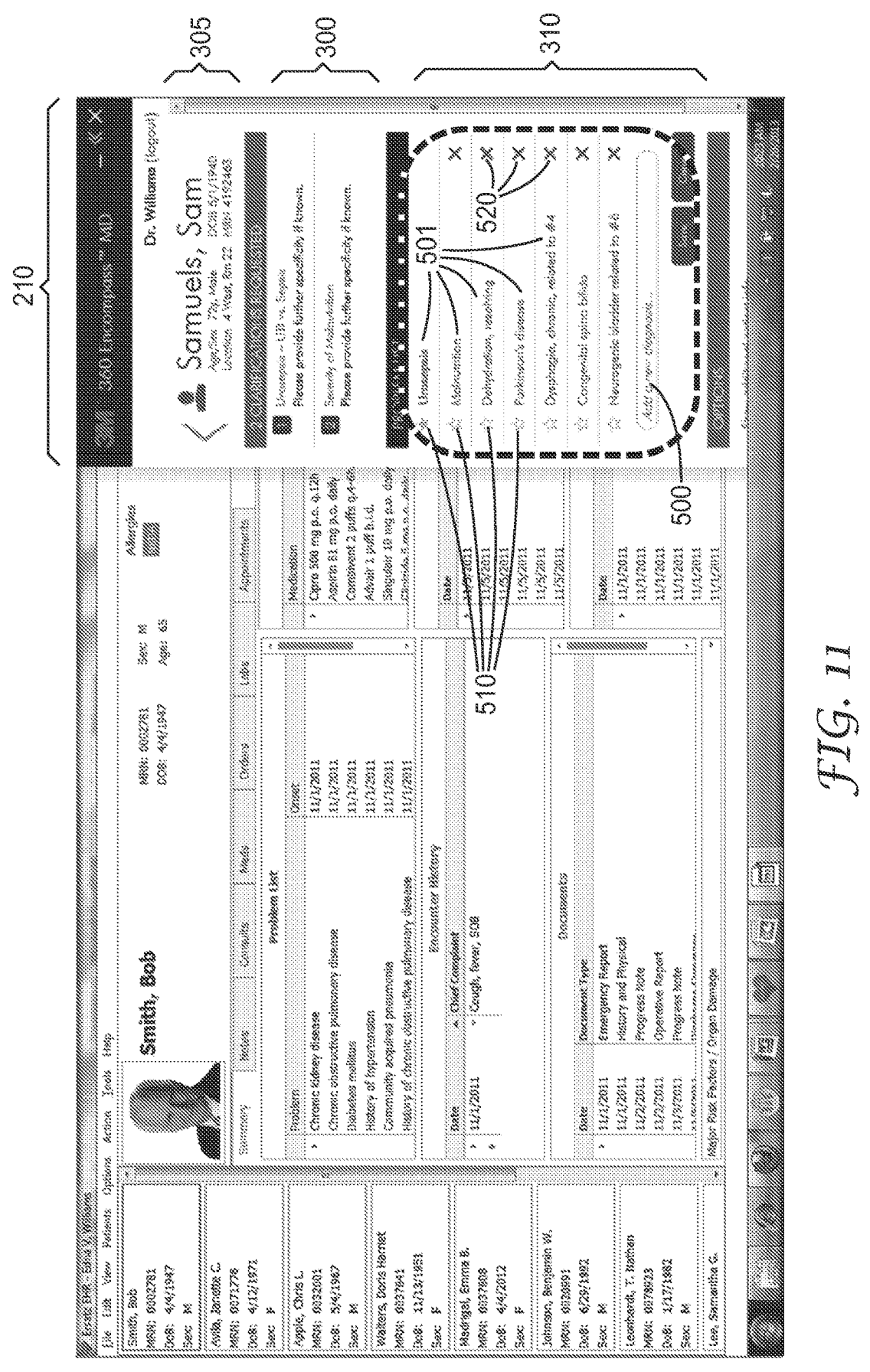

FIG. 11 shows another rendition of panel 210, but with user editable indicia associated with each of the entries 501 in the list 310 of potential medical problems. The user may edit list 310 by clicking anywhere in the problem list area. The user may re-order the problems within the list, delete problems (by selecting delete indicia 520), or add new problems by entering text associated therewith in text entry box 500. The natural language processing engine of the system may initially populate the list 310 with potential medical problems, but the system may require that the user finally approve and/or maintain the finalized list. For existing problem lists, the NLP engine may suggest further potential medical problems be added to the list. Such suggested problems may be associated with special visual indicia, such as highlighting, designed to signify that the problem is only suggested and has not been validated by the physician. Thus, NLP proposed problems in the list are shown with hollowed-out, or grayed, indicia 510, initially indicating that the proposed problem has not yet been validated by user. The user may signal his validation of the problem by selecting indicia 510 associated with certain of the problems with which the user agrees. In some examples, only signified problems may go into the resultant problem list.

FIG. 12 shows panel 210 with list 310 after the user has de-selected indicia 510 associated with "urosepsis" and instead selected indicia 550 associated with malnutrition. As shown in FIG. 12, the system has re-arranged list 310 with "Malnutrition" as the new top potential medical problem because indicia 550 was selected. In this manner, the user may re-arrange the potential medical problems of list 310. Instead of using indicia, the user may instead re-arrange problems within list 310 by selecting and dragging a problem to a different location within the list. FIG. 13 shows the resultant list 310 that includes the potential medical problems, with malnutrition being the only problem validated by the user. The validation of malnutrition is signified by indicia 550. The user may validate other problems as well by selecting associated indicia.

Figure 14:
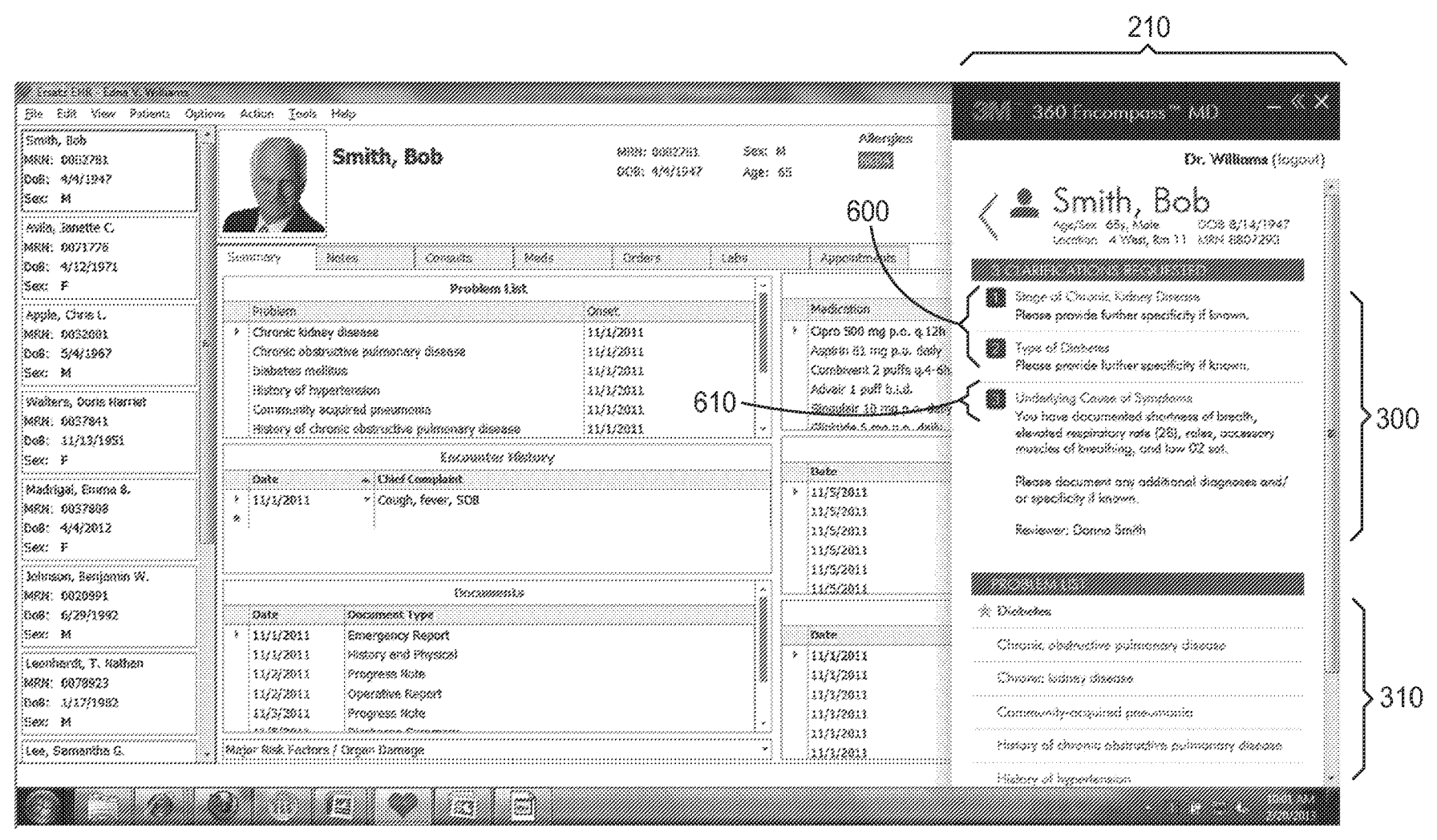

FIG. 14 shows another patient, that of Bob Smith, with queries generated by the CDI query system. Once again, query summaries 300 are shown in panel 210, and list 310 of the potential medical problems is shown for the patient. Queries 600 may include a list of selectable items. In contrast, query 610 may solicit additional documentation from the physician. As shown in the earlier example, the user may navigate into the first query and is presented with pick list 650, as shown in FIG. 15. FIG. 15 illustrates valid choices associated with the presented query, in this case query 640. Each item of pick list 650 is selectable to address the query 640. FIG. 16 shows pick list 650 and user selection indicia 660 associated with one of the valid choices presented to the user. Selection indicia 660 has been selected by the user to indicate selection of the associated item to address query 640, shown as a check mark. The item associated with selection indicia 660 may be representative of one or more undocumented items determined by the system.

FIG. 17 shows the second outstanding query 645 regarding patient Bob Smith. Once again, user is presented with pick list 650 upon selection of query 645. Pick list 650 presents valid choices associated with the presented query 645. FIG. 18 shows selection input associated with one of the valid choices of pick list 650, shown as the check mark in indicia 660. Selection of this item may address the query. A user may, in response to any of the queries generated by the CDI query system, select evidence indicia 710 which is shown in the options menu. Selection of evidence indicia 710 may transmit a request to a database to show evidence in the encounter-related documentation that may be relevant to the particular query (e.g., evidence from which the query was generated). The availability of pertinent evidence allows a physician to quickly view the source document or documents that led to this query being generated along with highlighting in those documents which pinpoints the specific words, terms, information or phrases that triggered this query. Typically, physicians rarely are alerted to the initial documentation and specific words or phrases in that documentation that was the cause of a query. This process of highlighting, for physicians, the words, terms and phrases that triggered the query may function as a feedback and training loop. The training, which may be similar to a spellchecker that highlights misspelled words, allows physicians to learn proper documentation in intuitive and real-life situations without outside human intervention.

Figure 19:
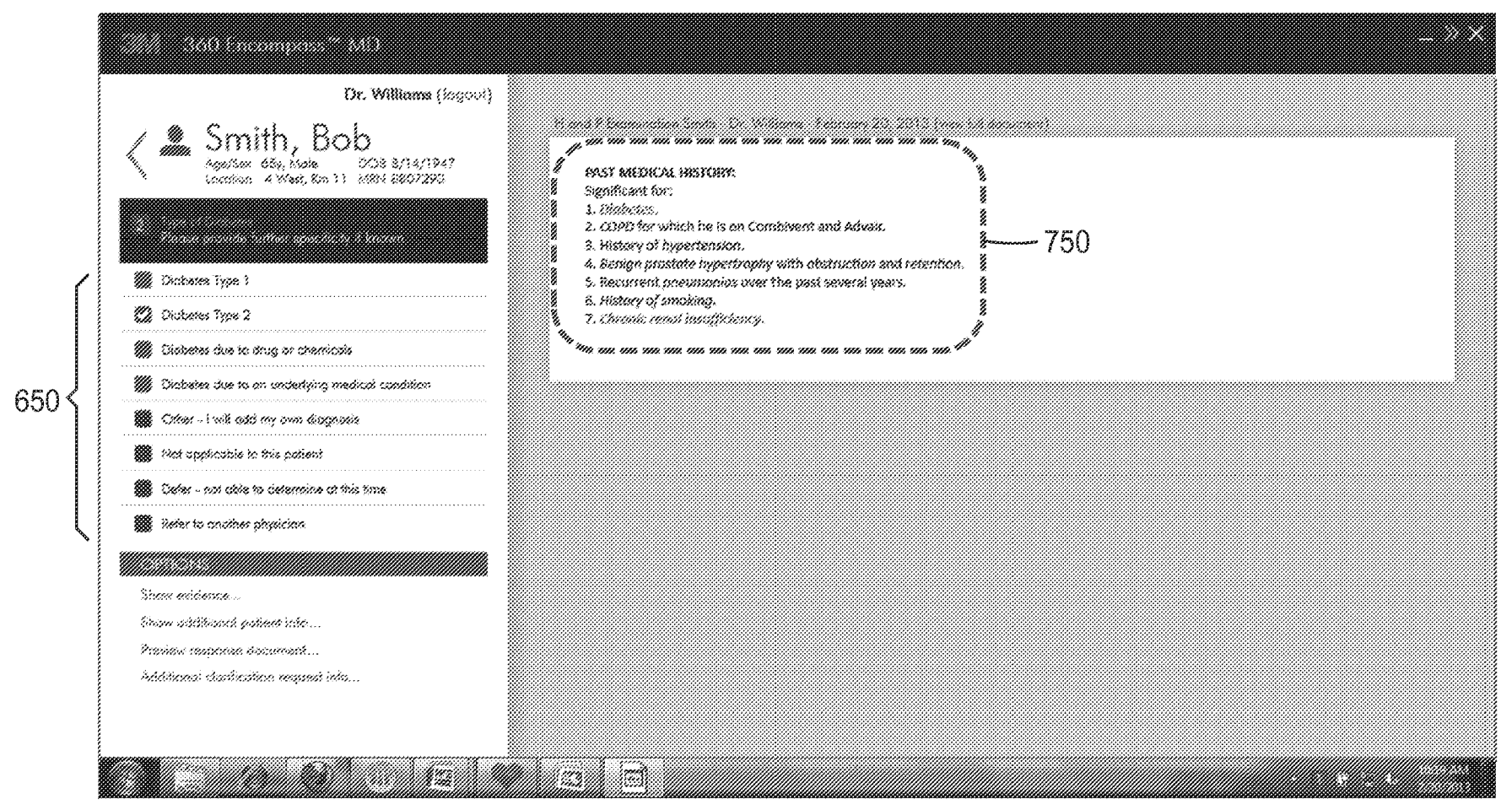

FIG. 19 shows a user interface that presents documentary evidence relevant to query 645 in FIG. 18. Panel 210 has been moved to the left portion of the screen, and the system displays evidence snippet 750 in the right panel of the user interface. In evidence snippet 750, the specific phrase that triggered this query (e.g., Chronic renal insufficiency) is highlighted to alert the physician to the specific portion of their documentation that the system identified as the evidence that triggered query 645. When viewing evidence snippet 750, the physician may then select one of the items of pick list 650 to address the query and allow the system to update the medical information.

Figure 20:
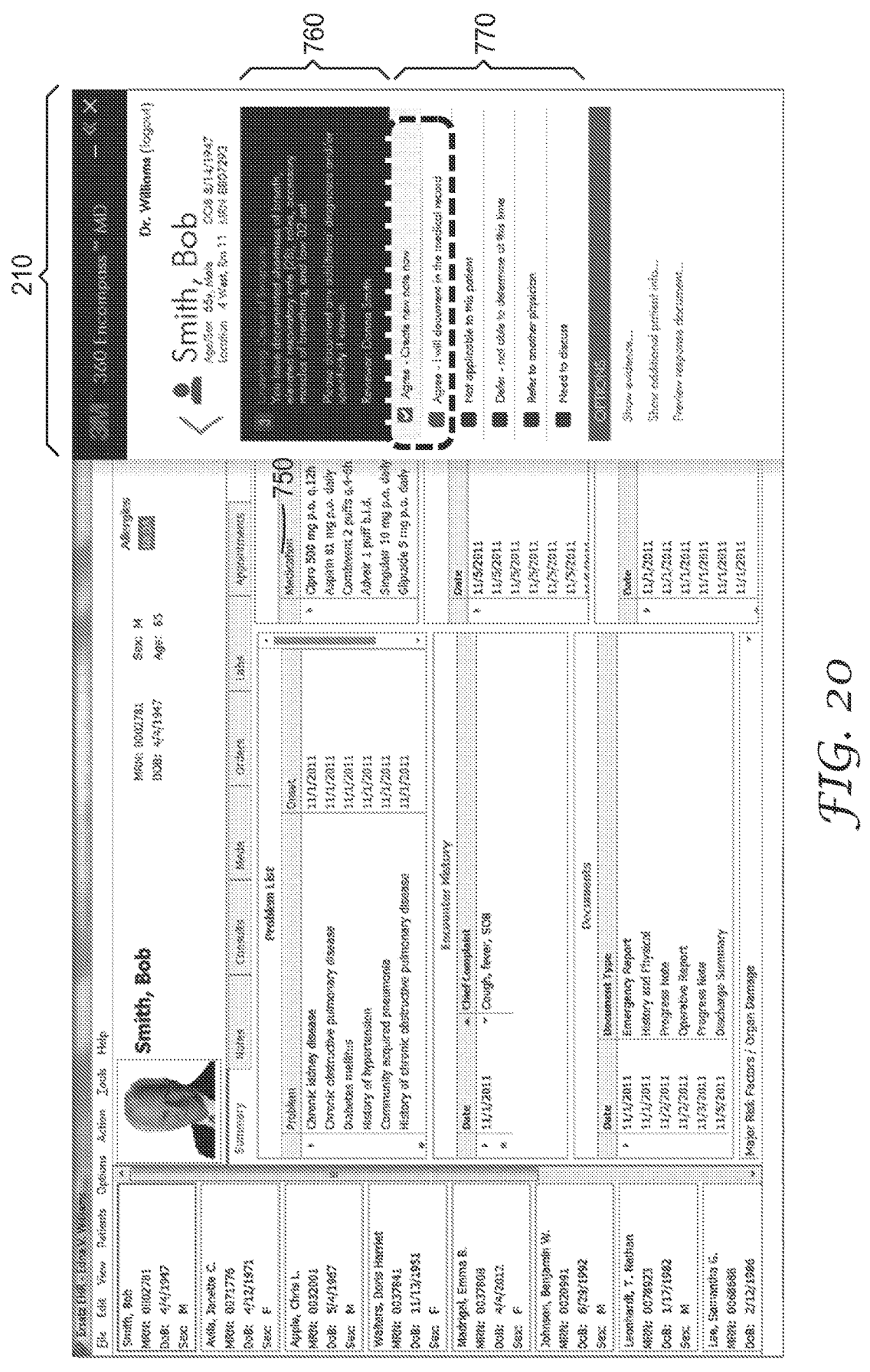
Figure 21:
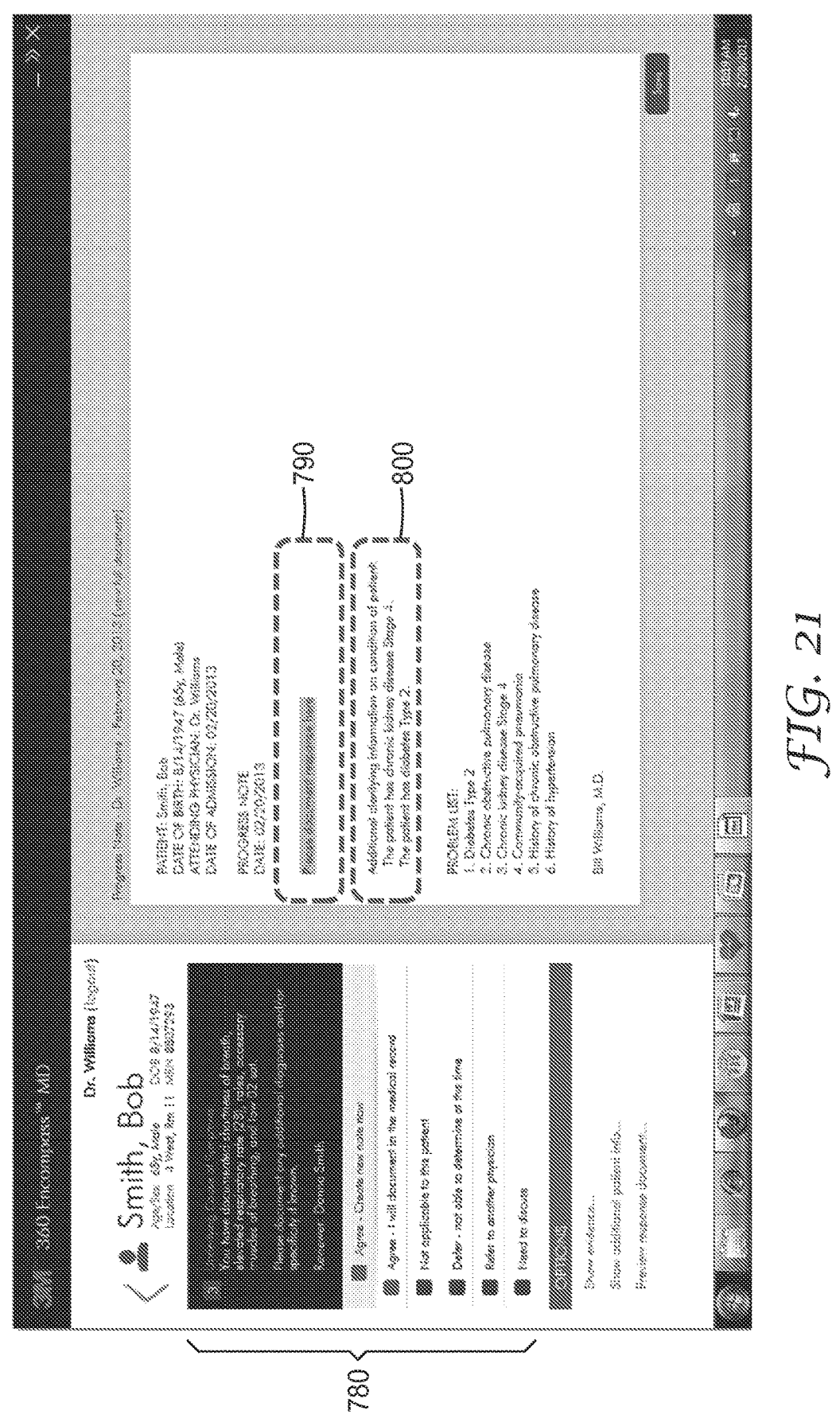

FIG. 20 shows panel 210 presenting the third query 760. Here, a specialist query from a CDI specialist is presented, and the user is presented with a pick list 770, several valid selections of which imply, or request, further text-based clarification from the physician. For example, the first option in the pick list 770 is "Agree—Create new note now". When a user selects this option, the CDI query system displays a response document as shown in FIG. 21, as described earlier, but the text area associated with the particular response (text area 790) highlighted to solicit user input in the form of text entry. Field 780 includes the pick list 770 and query 760. Text area 790 of the response document thus allows the physician to immediately respond to the specialist query with detailed information addressing the query. The system may require the user to type in their own response text (e.g., a custom response) for specialist queries (790), in contrast to CAPD queries where the system can auto-generate a response sentence for the physician. An auto-generated response sentence is shown as text area 800. Text area 800 shows the automated response sentences that are automatically inserted into the response document upon a physician selecting a response to a CAPD query. In this process, the physician only needs to select a choice from the multiple choice CAPD query response choices (e.g., selectable items), which results in pre-scripted response sentences being inserted into the response document. Upon approval by the physician (and subject to editing by physician, as needed), the response document may be uploaded as a new, signed document to the EHR. The scripted response selections may have been created by documentation improvement specialists, or according to standardized rules, to be compliant with all industry rules and regulations for querying physicians.

Figure 22:
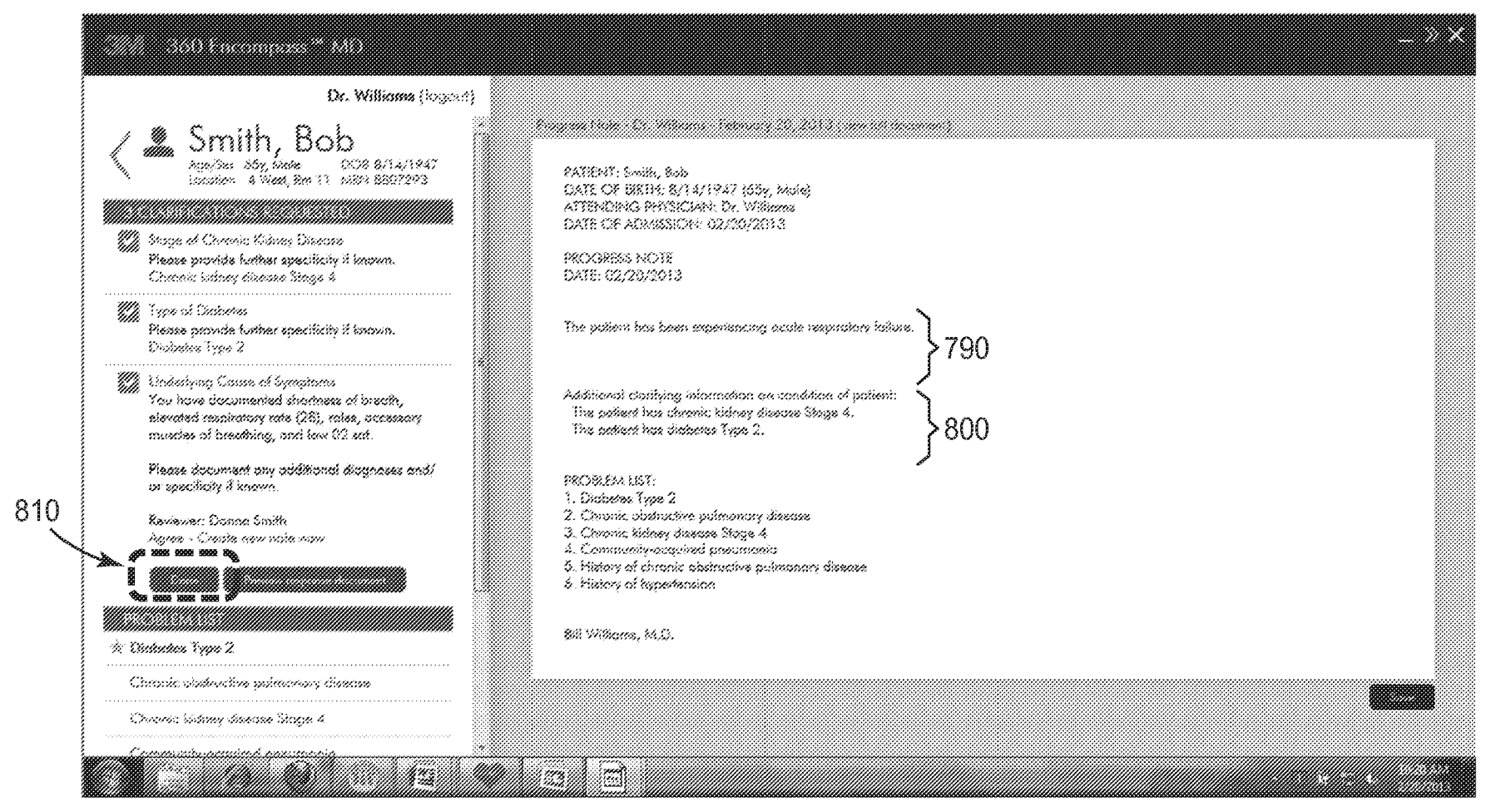

FIG. 22 shows the resultant response document from FIG. 21, with text area 790 completed. Text area 800 has been left unchanged by the physician as has the remainder of the response document. When the physician is satisfied with the answers to the query, the physician may select the done button 810 to submit the response document. The system may then process the responses to the queries and generate update information for addressing the missing or ambiguous information.

Figure 23:
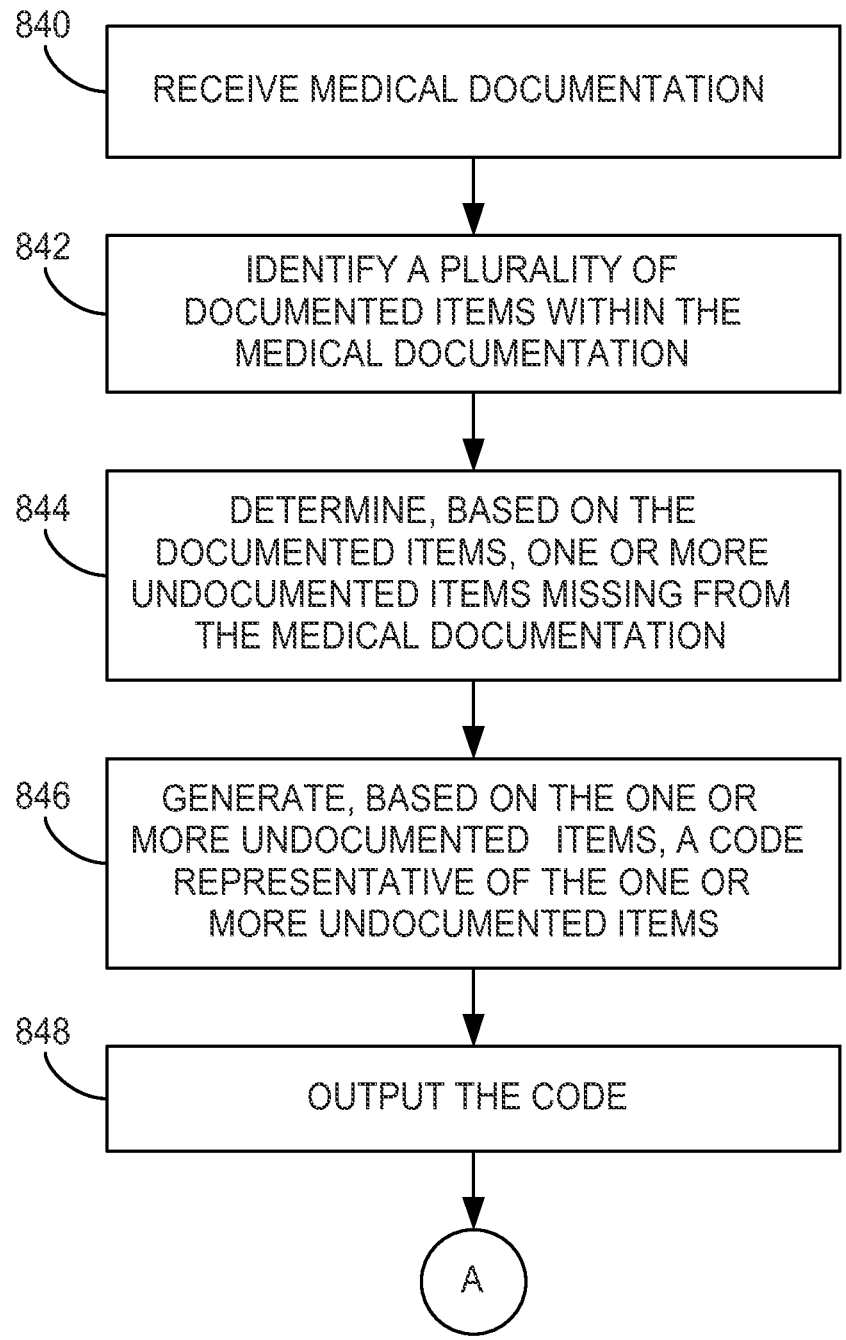
FIG. 23 is a flow diagram illustrating an example technique for determining undocumented items such as missing or ambiguous information from medical documentation.

FIG. 23 is a flow diagram illustrating an example technique for determining undocumented items such as missing or ambiguous information from medical documentation. FIG. 23 will be described from the perspective of server 4030 and repository 4040 of FIGS. 1D and 1E, although computing device 4100 of FIG. 1F, any other computing devices or systems (such as the systems described in FIG. 1A, 1B or 1C), or any combination thereof, may be used in other examples. As shown in FIG. 23, processor 5010 receives medical documentation from a physician and/or repository 4040 (840). Processor 5010 may execute NLP module 5060 to use natural language processing to identify a plurality of documented items within the medical documentation (842). The documented items may be words, phrases, or any other portion of the document associated with a medical concept.

Insufficiency module 5070 may receive the documented items and determine, based on the documented items, one or more undocumented items missing from the medical documentation (844). For example, insufficiency module 5070 may compare the documented items to predetermined sets of items contained in a database. Each of the predetermined sets of items may be associated with a medical concept, such as a concept related to a diagnosis, procedure, or treatment. Based on the comparison of the documented items to the predetermined sets of items, insufficiency module 5070 may identify one or more undocumented items that, when combined with one or more of the documented items, would indicate the medical concept. In this manner, insufficiency module 5070 may determine possible undocumented items or medical concepts that may be associated with the already created medical documentation.

Insufficiency module 5070 may generate, based on the one or more determined undocumented items, a code representative of the one or more undocumented items (846). This code may be representative of a medical concept including the undocumented items, or otherwise indicate possible missing or ambiguous information. Insufficiency module 5070 may then output the code for use in generating a query (848).

Figure 24:
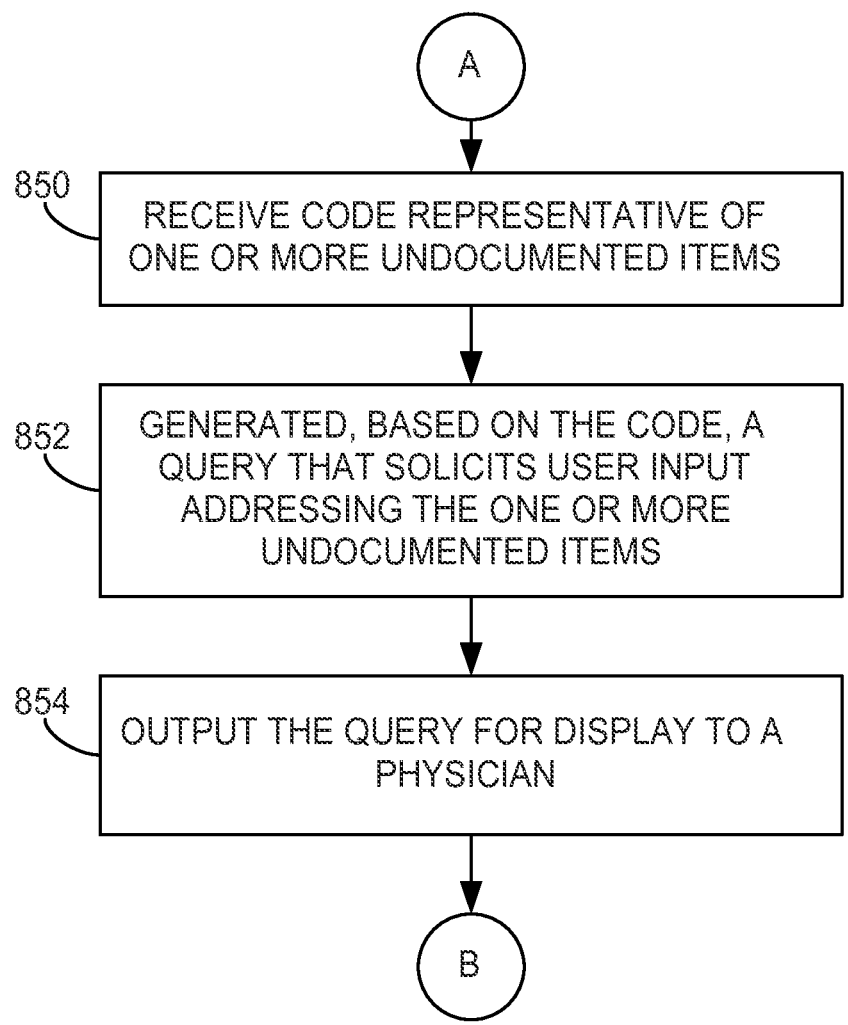
FIG. 24 is a flow diagram illustrating an example technique for generating a query that solicits user input addressing one or more undocumented items.

FIG. 24 is a flow diagram illustrating an example technique for generating a query that solicits user input addressing one or more undocumented items. The process of FIG. 24 may be a continuation of the process described in FIG. 23. FIG. 24 will be described from the perspective of server 4030 and repository 4040 of FIGS. 1D and 1E, although computing device 4100 of FIG. 1F, any other computing devices or systems (such as the systems described in FIG. 1A, 1B or 1C), or any combination thereof, may be used in other examples.

As shown in FIG. 24, query module 5090 receives a code representative of one or more undocumented items (850). Query module 5090 may receive the code from insufficiency module 5070 (indicator A connects the processes of block 848 of FIG. 23 and block 850 of FIG. 24) in some examples, or a different computing device in other examples. Since the one or more undocumented items may be associated with a respective medical concept that may be insufficiently documented in the analyzed medical documentation, the code may also be representative of the medical concept for which insufficiency module 5070 is attempting to clarify. Query module 5090 may then generate, based on the code, a query that solicits user input addressing the one or more undocumented items (852). Query module 5090 may then output the query for display to a physician via a user interface (854). For example, processor 5010 may transmit the query to client computing device 4010 of FIG. 1D for presentation to the physician.

The code may specify one or more aspects of the query. For example, the code may specify the particular medical concept, or concepts, the query is attempting to clarify. In addition, the code may specify whether the query can be clarified via a list of selectable items (e.g., pre-generated answers that address the query) or whether a text entry is required from the physician to address the query. Query module 5090 may incorporate other context of the patient, or physician preferences, or hospital preferences, to determine the selectable items within a generated query. For example, query module 5090 may generate the query based on one or more of the age and gender of the patient, patient treatment status, past query items that have been selected by the physician, hospital standards, or any other information. In this manner, query module 5090 may update the rules stored in query information 5140 in a learning process based on user input received addressing queries.

Figure 25:
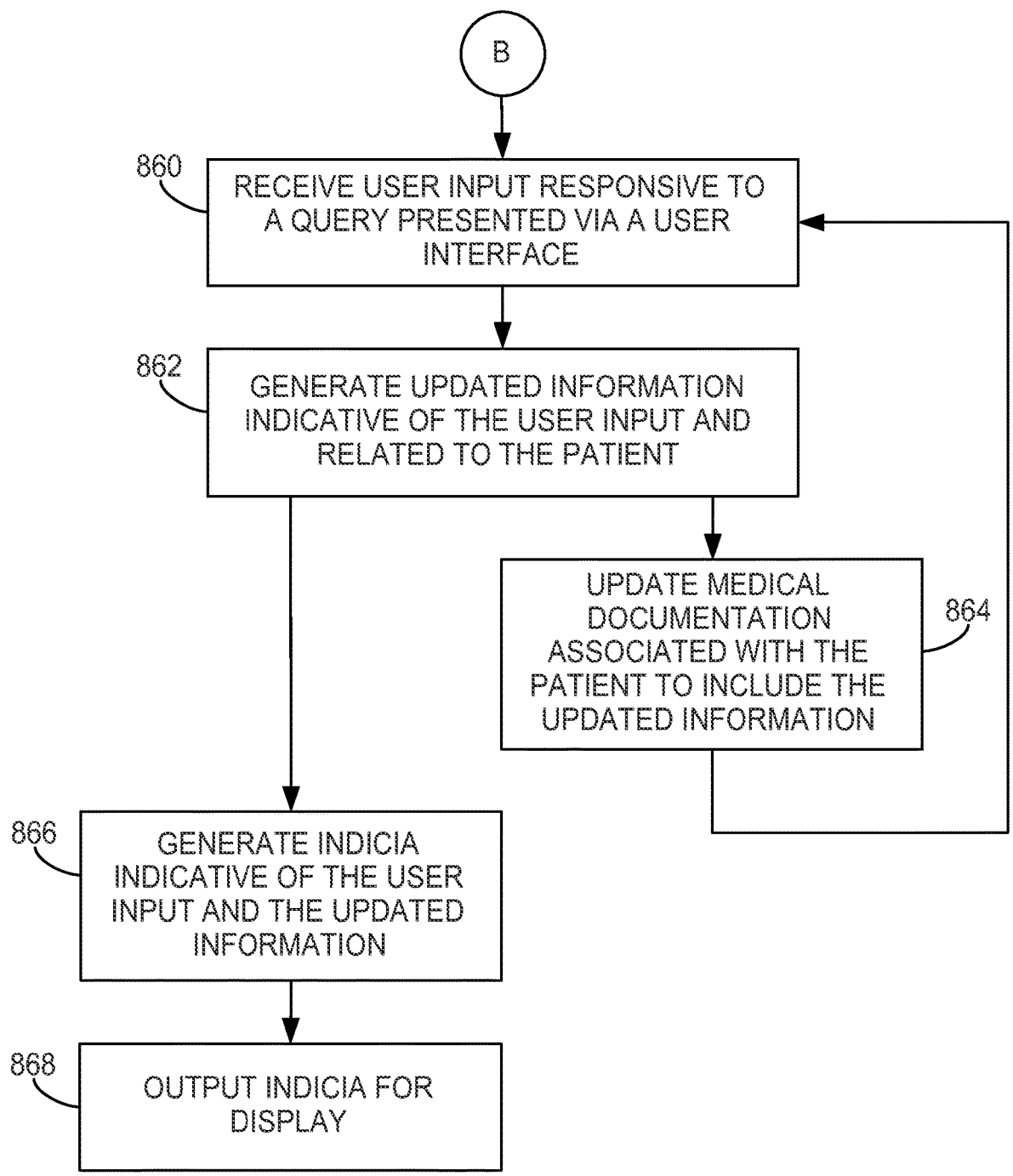
FIG. 25 is a flow diagram illustrating an example technique for generating updated information in response to receiving user input responsive to a presented query.

FIG. 25 is a flow diagram illustrating an example technique for generating updated information in response to receiving user input responsive to a presented query. The process of FIG. 25 may be a continuation of the process described in FIG. 24. FIG. 25 will be described from the perspective of server 4030 and repository 4040 of FIGS. 1D and 1E, although computing device 4100 of FIG. 1F, any other computing devices or systems (such as the systems described in FIG. 1A, 1B or 1C), or any combination thereof, may be used in other examples.

As shown in FIG. 25, processor 5010 receives an indication of user input responsive to a query presented via a user interface (860), and indicator B connects the processes of block 854 of FIG. 24 and block 860 of FIG. 25. In some examples, a client computing device (e.g., client computing device 4010) may receive the user input and transmit the indication of the input to server 4030 and processor 5010. In response to receiving the user input addressing the query, processor 5010 may execute feedback module 5100 to generate updated information indicative of the user input and related to the patient (862). For example, the updated information may include information associated with a selectable item selected from the query. The updated information may thus document a previously undocumented item or otherwise clarify whether or not a medical concept should be associated with the patient. In addition, updated information may include a response document created or modified by the physician.

In response to generating the updated information, feedback module 5100 may proceed to update medical documentation (e.g., medical documentation 5160 and/or the patient's EHR) associated with the patient to include the updated information (864). In some examples, processor 5010 may transmit a signal to another computing device requesting the medical documentation to be updated with the updated information. Processor 5010 may then receive additional user input responsive to additional queries, if applicable (860).

In addition, or alternative, to updating the medical documentation, feedback module 5100 may generate indicia indicative of the user input and the updated information (866) and output the indicia for display (868). Processor 5010 may transmit the indicia to client computing device 4010, for example, to be displayed to the physician within the user interface. For example, indicia may indicate which item within a query was selected by the physician, whether or not a query has been addressed, or even a new potential medical problem identified based on the updated information. In this manner, feedback module 5100 may provide indications to the user on the status of queries and/or actions that occurred based on the user input provided for the query. In some examples, server 4030 may receive follow-up user input based on the indicia and further modify the updated information based on the follow-up user input. For example, the physician may not agree with the outcome of the input provided to address the query, and the physician may provide additional, or modified, user input to fix the record of the patient.

Figure 26:
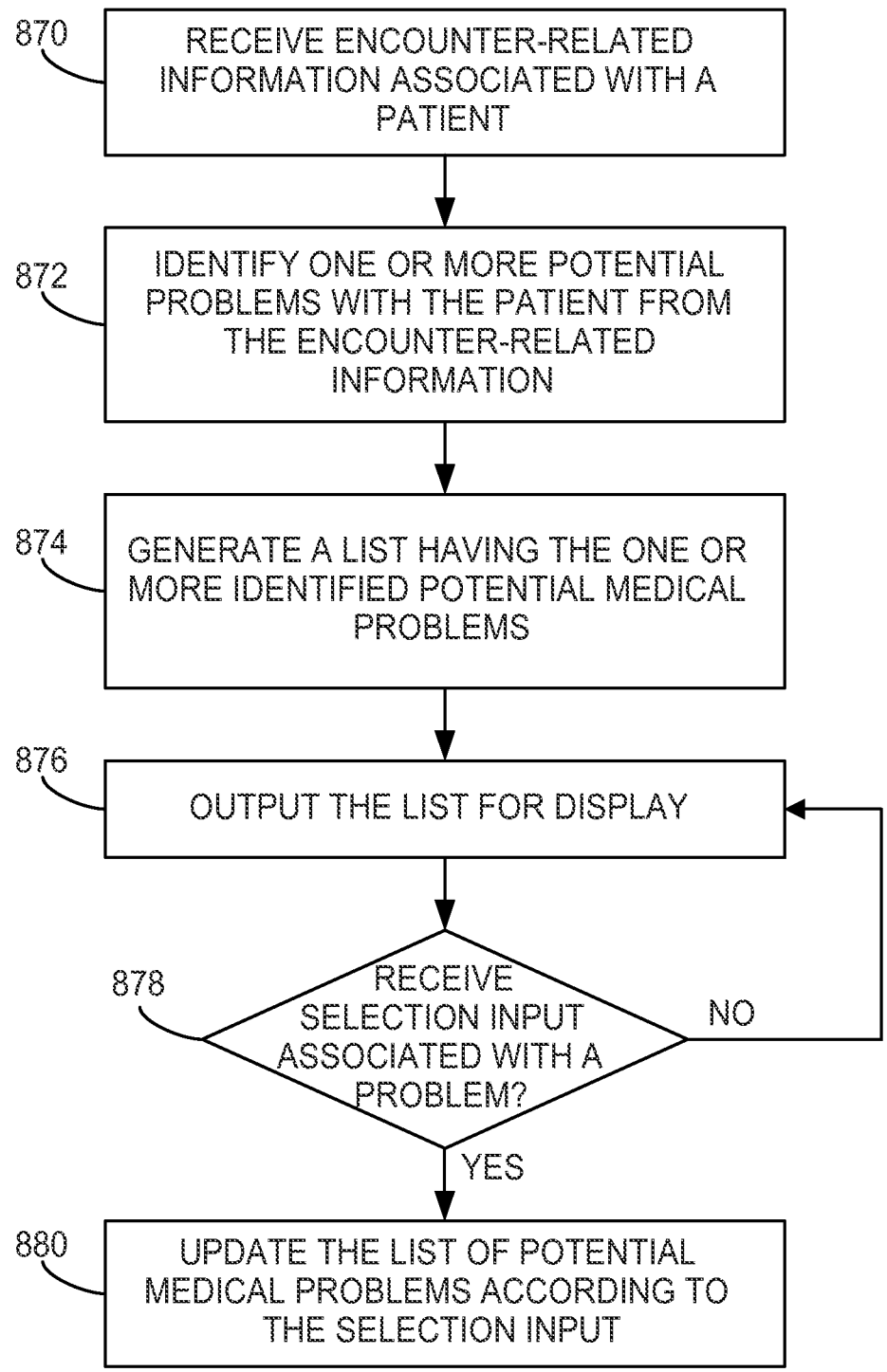
FIG. 26 is a flow diagram illustrating an example technique generating and updating a list of potential medical problems associated with a patient.

FIG. 26 is a flow diagram illustrating an example technique generating and updating a list of potential medical problems associated with a patient. FIG. 26 will be described from the perspective of server 4030 and repository 4040 of FIGS. 1D and 1E, although computing device 4100 of FIG. 1F, any other computing devices or systems (such as the systems described in FIG. 1A, 1B or 1C), or any combination thereof, may be used in other examples. Generating and updating a list of potential medical problems may be performed in addition, in combination with, or instead of, the generation and presentation of document insufficiency queries.

As shown in FIG. 26, processor 5010 may receive encounter-related information associated with a patient (870). The encounter-related information may be received from repository 4040, a different data storage device, or from the client computing device (e.g., client computing device 4010). Processor 5010 may execute problem list module 5080 to identify one or more potential medical problems with the patient from the encounter-related information (872). These potential medical problems may be auto-generated as suggestions of possible problems based on available documentation. Problem list module 5080 may then generate a list having the one or more identified potential medical problems (874). This generated list is different from a problem list maintained as part of the HER, or may be eventually used to populate the EHR problem list after confirmation and/or modification from the physician.

Problem list module 5080 then outputs the list for display, such as by an output device of client computing device 4010 (876). If processor 5010 does not receive an indication of selection input associated with one of the potential medical problems ("NO" branch of block 878), processor 5010 continues to output the list for display (876). If processor 5010 receives an indication of selection input associated with one of the potential medical problems ("YES" branch of block 878), processor 5010 may control problem list module 5080 to update the list of potential medical problems according to the selection input (880). For example, selection input may include confirmation that a potential medical problem is an actual problem associated with the patient. Selection input may instead discard a potential medical problem as an actual problem or modify or clarify a potential medical problem. Problem list module 5080 may update the EHR problem list, or request updating of the EHR problem list, in response to receiving confirmation from the physician that a potential medical problem is an actual problem.

The following examples illustrate example methods, devices, and systems described herein. Example 1: a computer-implemented method for determining insufficient medical information associated with a patient, the method including receiving, by a computing device, documentation comprising a plurality of documented items related to the patient, determining, by the computing device and based on at least a subset of the plurality of documented items, one or more undocumented items missing from the documentation, wherein the subset of the plurality of documented items and at least one of the one or more undocumented items define a medical concept, generating, by the computing device and based on the one or more undocumented items, a code representative of the one or more undocumented items, and outputting, by the computing device, the code.

Example 2: the method of example 1, wherein the medical concept comprises one of a patient condition, a diagnosis of the patient, or a medical procedure performed on the patient.

Example 3: the method of any of examples 1 and 2, wherein determining the one or more undocumented items comprises comparing the subset of the plurality of documented items to one or more predetermined sets of items, identifying, based on the comparison, at least one of the one or more predetermined sets of items that comprises each documented item of the subset, and selecting, for each of the identified at least one predetermined sets of items, at least one item not included in the subset as at least one of the one or more undocumented items.

Example 4: the method of any of examples 1-3, wherein the medical concept is one of a plurality of medical concepts, the one or more undocumented items comprise a plurality of undocumented items, and each of the plurality of undocumented items are associated with a different one of the plurality of medical concepts.

Example 5: the method of any of examples 1-4, wherein at least one of the one or more undocumented items completes, with the subset of the plurality of documented items, a specific medical concept.

Example 6: the method of any of examples 1-5, wherein the medical concept is a first medical concept, at least one of the one or more undocumented items links a second medical concept and a third medical concept to the first medical concept, and the second medical concept and the third medical concepts are defined by at least some of the plurality of documented items.

Example 7: the method of any of examples 1-6, wherein at least one of the one or more undocumented items confirms the medical concept, and wherein the medical concept was previously indicated and unconfirmed by the subset of the plurality of documented items.

Example 8, the method of any of examples 1-7, further comprising, responsive to receiving the code, generating, based on the code and for display, a query presenting at least one of the one or more undocumented items for selection by a user.

Example 9: a computerized system for coding medical documentation, the system comprising one or more computing devices configured to receive documentation comprising a plurality of documented items related to the patient, determine, based on at least a subset of the plurality of documented items, one or more undocumented items missing from the documentation, wherein the subset of the plurality of documented items and at least one of the one or more undocumented items define a medical concept, generate, based on the one or more undocumented items, a code representative of the one or more undocumented items, and output the code.

Example 10: the system of example 9, wherein the medical concept comprises one of a patient condition, a diagnosis of the patient, or a medical procedure performed on the patient.

Example 11: the system of any of examples 9 and 10, wherein the one or more computing devices are configured to determine the one or more undocumented items by comparing the subset of the plurality of documented items to one or more predetermined sets of items, identifying, based on the comparison, at least one of the one or more predetermined sets of items that comprises each documented item of the subset, and selecting, for each of the identified at least one predetermined sets of items, at least one item not included in the subset as at least one of the one or more undocumented items.

Example 12: the system of any of examples 9-11, wherein the medical concept is one of a plurality of medical concepts, the one or more undocumented items comprise a plurality of undocumented items, and each of the plurality of undocumented items are associated with a different one of the plurality of medical concepts.

Example 13: the system of any of examples 9-12, wherein at least one of the one or more undocumented items completes, with the subset of the plurality of documented items, a specific medical concept.

Example 14: the system of any of examples 9-13, wherein the medical concept is a first medical concept, at least one of the one or more undocumented items links a second medical concept and a third medical concept to the first medical concept, and the second medical concept and the third medical concepts are defined by at least some of the plurality of documented items.

Example 15: the system of any of examples 9-14, wherein at least one of the one or more undocumented items confirms the medical concept, and wherein the medical concept was previously indicated and unconfirmed by the subset of the plurality of documented items.

Example 16: the system of any of examples 9-15, wherein the one or more computing devices are configured to, responsive to receiving the code, generate, based on the code and for display, a query presenting at least one of the one or more undocumented items for selection by a user.

Example 17: the system of any of examples 9-16, wherein the one or more computing devices comprises a documentation insufficiency coding module configured to receive the documentation comprising a plurality of documented items related to the patient, determine, based on the at least a subset of the plurality of documented items, one or more undocumented items missing from the documentation, and generate, based on the one or more undocumented items, the code representative of the one or more undocumented items.

Example 18: a computer-readable storage medium comprising instructions that, when executed, cause one or more processors to receive documentation comprising a plurality of documented items related to the patient, determine, based on at least a subset of the plurality of documented items, one or more undocumented items missing from the documentation, wherein the subset of the plurality of documented items and at least one of the one or more undocumented items define a medical concept; generate, based on the one or more undocumented items, a code representative of the one or more undocumented items, and output the code.

Example 19: the computer-readable storage medium of example 18, wherein the medical concept comprises one of a patient condition, a diagnosis of the patient, or a medical procedure performed on the patient.

Example 20: the computer-readable storage medium of any of examples 18 and 19, wherein the instructions that cause the one or more processors to determine the one or more undocumented items comprise instructions that cause the one or more processors to compare the subset of the plurality of documented items to one or more predetermined sets of items, identify, based on the comparison, at least one of the one or more predetermined sets of items that comprises each documented item of the subset, and select, for each of the identified at least one predetermined sets of items, at least one item not included in the subset as at least one of the one or more undocumented items.

Example 21: the computer-readable storage medium of any of examples 18-20, further comprising instructions that cause the one or more processors to, responsive to receiving the code, generate, based on the code and for display, a query presenting at least one of the one or more undocumented items for selection by a user.

Example 22: a computer-implemented method for requesting medical information associated with a patient, the method comprising receiving, by a computing device, a code representative of one or more undocumented items determined from a plurality of documented items related to the patient, generating, by the computing device and based on the code, a query that solicits user input addressing the one or more undocumented items, and outputting, by the computing device and for display, the query.

Example 23: the method of example 22, further comprising presenting, via a display device, a user interface comprising the query.

Example 24: the method of any of examples 22 and 23, wherein the query comprises one or more selectable items that, when selected, addresses the one or more undocumented items.

Example 25: the method of any of examples 22-24, wherein at least one of the one or more selectable items corresponds to a respective one of the one or more undocumented items, and wherein selection of one of the selectable items addresses the one or more undocumented items represented by the code.

Example 26: the method of any of examples 22-25, wherein one of the one or more selectable items comprises a rejection input that rejects all of the one or more selectable items corresponding to the respective one of the one or more undocumented items, and wherein selection of the rejection input addresses the one or more undocumented items represented by the code.

Example 27: the method of any of examples 22-26, wherein the query comprises one of a question or a statement, and wherein the method further comprises receiving, via the user interface, a query response that is responsive to either the question or the statement.

Example 28: the method of any of examples 22-27, further comprising updating, based on the query response to the presented query, documentation associated with the patient to define one or more medical concepts.

Example 29: the method of any of examples 22-28, further comprising presenting, via the user interface, the query with a problem list associated with the patient, and wherein user input solicited by the query triggers an update to the problem list.

Example 30: the method of any of examples 22-29, wherein the query is one of a plurality of queries associated with one or more respective undocumented items, and wherein the method further comprises generating, for display in association with the patient, indicia representative of a number of the plurality of queries requiring a respective response.

Example 31: the method of any of examples 22-30, further comprising generating, based on at least a portion of encounter-related information associated with the patient, medical evidence associated with the patient and outputting, for display with the query, at least a portion of the medical evidence.

Example 32: the method of any of examples 22-31, wherein the user is a physician.

Example 33: a computerized system for requesting medical documentation associated with a patient, the system comprising one or more computing devices configured to receive a code representative of one or more undocumented items determined from a plurality of documented items related to the patient, generate, based on the code, an query that solicits user input addressing the one or more undocumented items, and output, for display, the query.

Example 34: the system of example 33, wherein the one or more computing devices are configured to present, via a display device, a user interface comprising the query.

Example 35: the system of any of examples 33-34, wherein the query comprises one or more selectable items that, when selected, addresses the one or more undocumented items.

Example 36: the system of any of examples 33-35, wherein at least one of the one or more selectable items corresponds to a respective one of the one or more undocumented items, and wherein selection of one of the selectable items addresses the one or more undocumented items represented by the code.

Example 37: the system of any of examples 33-36, wherein one of the one or more selectable items comprises a rejection input that rejects all of the one or more selectable items corresponding to the respective one of the one or more undocumented items, and wherein selection of the rejection input addresses the one or more undocumented items represented by the code.

Example 38: the system of any of examples 33-37, wherein the query comprises one of a question or a statement, and wherein the method further comprises receiving, via the user interface, a query response that is responsive to either the question or the statement.

Example 39: the system of any of examples 33-38, wherein the one or more computing devices are configured to update, based on the query response to the presented query, documentation associated with the patient to define one or more medical concepts.

Example 40: the system of any of examples 33-39, wherein the one or more computing devices are configured to present, via the user interface, the query with a problem list associated with the patient, and wherein user input solicited by the query triggers an update to the problem list.

Example 41: the system of any of examples 33-40, wherein the query is one of a plurality of queries associated with one or more respective undocumented items, and wherein the one or more computing devices are configured to generate, for display in association with the patient, indicia representative of a number of the plurality of queries requiring a respective response.

Example 42: the system of any of examples 33-41, wherein the one or more computing devices are configured to generate, based on at least a portion of encounter-related information associated with the patient, medical evidence associated with the patient and output, for display with the query, at least a portion of the medical evidence.

Example 43: the system of any of examples 33-42, wherein the one or more computing devices comprise a query generation module configured to receive the code representative of the one or more undocumented items and generate, based on the code, the query that solicits user input addressing the one or more undocumented items.

Example 44: the system of any of examples 33-43, wherein the user is a physician.

Example 45: a computer-readable storage medium comprising instructions that, when executed, cause one or more processors to receive a code representative of one or more undocumented items determined from a plurality of documented items related to the patient, generate, based on the code, an query that solicits user input addressing the one or more undocumented items, and output, for display, the query.

Example 46: the computer-readable storage medium of example 45, further comprising instructions that cause the one or more processors to present, via a display device, a user interface comprising the query.

Example 47: the computer-readable storage medium of any of examples 45 and 46, wherein the query comprises one of a question or a statement, and wherein the computer-readable storage medium comprises instructions that cause one or more processors to receive, via the user interface, a query response that is responsive to either the question or the statement.

Example 48: a computer-implemented method for managing medical documentation associated with a patient, the method comprising receiving, by a computing device, user input responsive to a query presented via a user interface, wherein the user input addresses one or more undocumented items related to the query and determined from a plurality of documented items related to the patient, responsive to receiving the user input, generating, by the computing device, updated information indicative of the user input and related to the patient, generating, by the computing device, indicia indicative of the user input, and outputting, for display, the indicia.

Example 49: the method of example 48, further comprising updating the medical documentation associated with the patient to include the updated information.

Example 50: the method of any of examples 48 and 49, wherein the indicia comprises a textual representation indicative of the updated information that addresses the one or more undocumented items, and wherein the method further comprises receiving user input approving the textual representation.

Example 51: the method of any of examples 48-50, wherein the user input approving the textual representation comprises an electronic signature from a user that provided the user input responsive to the query.

Example 52: the method of any of examples 48-51, wherein receiving user input approving the textual representation comprises receiving modification user input, the modification user input in the form of one or more edits to the textual representation, and wherein the method further comprises modifying, based on the edits to the textual representation, the updated information.

Example 53: the method of any of examples 48-52, further comprising, responsive to receiving the user input approving the textual representation, associating the updated information with the medical documentation.

Example 54: the method of any of examples 48-53, wherein the medical documentation comprises the plurality of documented items related to the patient, and wherein the method further comprises updating, based on the user input responsive to the query, the medical documentation associated with the patient to define one or more additional medical concepts.

Example 55: the method of any of examples 48-54, wherein the computing device is a first computing device, and the method further comprises generating a request to update the medical documentation associated with the patient with the updated information and transmitting, from the first computing device, the request to a second computing device that maintains the medical documentation.

Example 56: the method of any of examples 48-55, further comprising presenting, via a display device, a user interface comprising the query, receiving, via the user interface, the user input responsive to the query, and presenting, via the display device, the user interface comprising the indicia.

Example 57: the method of any of examples 48-56, further comprising presenting, via the user interface, the query and a problem list associated with the patient and responsive to receiving the user input, updating, based on the user input, the problem list.

Example 58: the method of any of examples 49-57, wherein the user input comprises a selection input of one or more selectable items of the query that, when selected, address the one or more undocumented items.

Example 59: the method of any of examples 49-58, wherein the user input comprises textual input addressing the one or more undocumented items.

Example 60: the method of any of examples 49-59, wherein the user input is provided by a physician.

Example 61: a computerized system for managing medical documentation associated with a patient, the system comprising one or more computing devices configured to receive user input responsive to a query presented via a user interface, wherein the user input addresses one or more undocumented items related to the query and determined from a plurality of documented items related to the patient, responsive to receiving the user input, generate updated information indicative of the user input and related to the patient, generate indicia indicative of the user input, and output, for display, the indicia.

Example 62: the system of example 61, wherein the one or more computing devices are configured to update the medical documentation associated with the patient to include the updated information.

Example 63: the system of any of examples 61 and 62, wherein the indicia comprises a textual representation indicative of the updated information that addresses the one or more undocumented items, and wherein the one or more computing devices are configured to receive user input approving the textual representation.

Example 64: the system of any of examples 61-63, wherein the user input approving the textual representation comprises an electronic signature from a user that provided the user input responsive to the query.

Example 65: the system of any of examples 61-64, wherein receiving user input approving the textual representation comprises receiving modification user input, the modification user input in the form of one or more edits to the textual representation, and wherein the one or more computing devices are configured to modify, based on the edits to the textual representation, the updated information.

Example 66: the system of any of examples 61-65, wherein the one or more computing devices are configured to, responsive to receiving the user input approving the textual representation, associate the updated information with the medical documentation.

Example 67: the system of any of examples 61-66, wherein the medical documentation comprises the plurality of documented items related to the patient, and wherein the one or more computing devices are configured to update, based on the user input responsive to the query, the medical documentation associated with the patient to define one or more additional medical concepts.

Example 68: the system of any of examples 61-67, wherein the one or more computing devices are configured to generate a request to update the medical documentation associated with the patient with the updated information and transmit, from the one or more computing devices, the request to a computing system that maintains the medical documentation.

Example 69: the system of any of examples 61-68, further comprising a display device configured to present a user interface comprising the query, and wherein the one or more computing devices are configured to receive, via the user interface, the user input responsive to the query and the display device is configured to present the user interface comprising the indicia.

Example 70: the system of any of examples 61-69, wherein the display device is configured to present, via the user interface, the query and a problem list associated with the patient, and the one or more computing devices are configured to, responsive to receiving the user input, update, based on the user input, the problem list.

Example 71: the system of any of examples 61-70, wherein the user input comprises a selection input of one or more selectable items of the query that, when selected, address the one or more undocumented items.

Example 72: the system of any of examples 61-71, wherein the user input comprises textual input addressing the one or more undocumented items.

Example 73: the system of any of examples 61-72, wherein the user input is provided by a physician.

Example 74: the system of any of examples 61-73, wherein the one or more computing devices comprise a first module configured to generate the updated information indicative of the user input and related to the patient and a second module configured to generate the indicia indicative of the user input.

Example 75: a computer-readable storage medium comprising instructions that, when executed, cause one or more processors to receive user input responsive to a query presented via a user interface, wherein the user input addresses one or more undocumented items related to the query and determined from a plurality of documented items related to the patient, responsive to receiving the user input, generate updated information indicative of the user input and related to the patient, generate indicia indicative of the user input, and output, for display, the indicia.

Example 76: a computer implemented method of managing medical information associated with a patient, the method comprising identifying, by a computing device, one or more potential medical problems with the patient from encounter-related information associated with the patient, generating, by the computing device, a list comprising the one or more potential medical problems, outputting, by the computing device and for display, the list, receiving, by the computing device, an indication of selection input from a user and associated with at least one of the potential medical problems, and updating, by the computing device, the list of potential medical problems according to the indication of the selection input.

Example 77: the method of example 76, further comprising presenting, by a display device, the list of the one or more potential medical problems in a user interface, receiving, by an input device, the selection input from the user, and generating, by the input device, the indication of the selection input.

Example 78: the method of any of examples 76 and 77, further comprising generating, by the computing device, a signal to update a problem list consistent with the received selection input, wherein the problem list is different from the list of one or more potential problems, and wherein the problem list is maintained as part of an electronic health record associated with the patient.

Example 79: the method of any of examples 76-78, further comprising transmitting, by the computing device, the signal to a computing system that stores the electronic health record associated with the patient.

Example 80: the method of any of examples 76-79, further comprising updating, according to the signal, the electronic health record associated with the patient.

Example 81: the method of any of examples 76-80, wherein the signal comprises information consistent with an HL7 standard or a Clinical Document Architecture standard.

Example 82: the method of any of examples 76-81, further comprising, prior to outputting the list, presenting, via a display device, visual indicia indicative of the one or more potential problems having been identified.

Example 83: the method of any of examples 76-82, wherein identifying the one or more potential medical problems comprises reviewing, by a natural language processing engine, the encounter-related information associated with the patient and identifying, by a problem list identification engine, the one or more potential medical problems from the encounter-related information.

Example 84: the method of any of examples 76-83, wherein the user is a physician.

Example 85: the method of any of examples 76-84, further comprising receiving an indication of edit input from the user that edits one of the one or more potential medical problems and updating the one of the one or more potential medical problems according to the edit input.

Example 86: the method of any of examples 76-85, wherein the edit input comprises a request to eliminate the one of the one or more potential medical problems from the list.

Example 87: the method of any of examples 76-86, further comprising receiving validation-related user input from the user, wherein the validation-related user input indicates user acceptance of the one or more potential medical problems of the list as being representative of current medical problems associated with the patient.

Example 88: the method of any of examples 76-87, further comprising generating a response document consistent with the selection input, the response document memorializing the validation of the at least one of the potential medical problems.

Example 89: a computerized system for managing medical information associated with a patient, the system comprising one or more computing devices configured to identify one or more potential medical problems with the patient from encounter-related information associated with the patient, generate a list comprising the one or more potential medical problems, output, for display, the list, receive an indication of selection input from a user and associated with at least one of the potential medical problems, and update the list of potential medical problems according to the indication of the selection input.

Example 90: the system of example 89, further comprising a display device configured to present the list of the one or more potential medical problems in a user interface and an input device configured to receive the selection input from the user and generate the indication of the selection input.

Example 91: the system of any of examples 89 and 90, wherein the one or more computing devices are configured to generate a signal to update a problem list consistent with the received selection input, wherein the problem list is different from the list of one or more potential problems, and wherein the problem list is maintained as part of an electronic health record associated with the patient.

Example 92: the system of any of examples 89-91, wherein the one or more computing devices are configured to transmit, via a communication unit, the signal to a computing system configured to store the electronic health record associated with the patient.

Example 93: the system of any of examples 89-92, wherein the one or more computing devices are configured to update, according to the signal, the electronic health record associated with the patient.

Example 94: the system of any of examples 89-93, wherein the signal comprises information consistent with an HL7 or a Clinical Document Architecture standard.

Example 95: the system of any of examples 89-94, wherein the one or more computing devices are configured to, prior to outputting the list, output, for presentation via a display device, visual indicia indicative of the one or more potential problems having been identified.

Example 96: the system of any of examples 89-95, wherein the one or more computing devices are configured to identify the one or more potential medical problems by reviewing, via a natural language processing engine, the encounter-related information associated with the patient and identifying, via a problem list identification engine, the one or more potential medical problems from the encounter-related information.

Example 97: the system of any of examples 89-96, wherein the user is a physician.

Example 98: the system of any of examples 89-97, wherein the one or more computing devices are configured to receive an indication of edit input from the user that edits one of the one or more potential medical problems and update the one of the one or more potential medical problems according to the edit input.

Example 99: the system of any of examples 89-98, wherein the edit input comprises a request to eliminate the one of the one or more potential medical problems from the list.

Example 100: the system of any of examples 89-98, wherein the one or more computing devices are configured to receive validation-related user input from the user, wherein the validation-related user input indicates user acceptance of the one or more potential medical problems of the list as being representative of current medical problems associated with the patient.

Example 101: the system of any of examples 89-99, wherein the one or more computing devices are configured to generate a response document consistent with the selection input, the response document memorializing the validation of the at least one of the potential medical problems.

Example 102: the system of any of examples 89-100, wherein the one or more computing devices comprise a natural language processing module configured to identify the one or more potential medical problems from encounter-related information and a problem list identification module configured to generate the list.

Example 103: a computer-readable storage medium comprising instructions that, when executed, cause one or more processors to identify one or more potential medical problems with the patient from encounter-related information associated with the patient, generate a list comprising the one or more potential medical problems, output, for display, the list, receive an indication of selection input from a user and associated with at least one of the potential medical problems, and update the list of potential medical problems according to the indication of the selection input.

Example 104: a computer implemented method that uses one or more processors of a computer system to automatically reviewing patient encounter-related information to identify missing or unclear information, retrieve a query to solicit information from a user that will address the missing information or that will clarify the unclear information, present the query in a user interface of a computer system, receive a query response from the user, and automatically generate update indicia indicative of the query response. In some examples, the update indicia comprises a textual representation of the query response, the update indicia comprises a textual representation of unclear information that was clarified with the query response. In other examples, the query comprises a question or statement, as well as a plurality of choices responsive to the question or statement. The query response from the user may comprise selection input associated with one of the plurality of choices. The selection input may comprise input associated with a pointing device. The pointing device may be a touch sensor. The method may include presenting the textual representation in a further user interface and receiving approval input from the user, the approval input associated with the textual representation. The approval input may comprise the user providing selection input with a visual indicium in the further user interface that is associated with approval. The approval input may comprise an electronic signature by the user. The method may include receiving modification feedback from the user, the modification feedback in the form of edits made by the user to the presented textual representation. The method may include, once the approval input has been received, associating the textual representation with the patient encounter-related information. The automatically reviewing may be done by an NLP engine. The method may include generating in the user interface evidence for the query, the evidence being portions of the encounter-related information. The evidence may be presented as part of the query. Systems and devices may perform these methods.

Example 105: a computer implemented method of maintaining a problem list associated with a patient, comprising automatically reviewing patient encounter-related information to identify potential problems associated with the patient, presenting, in a user interface of a computer system, a listing of the potential problems, receiving, from a user, selection input associated with at least one of the potential problems, and providing signals for updating the problem list consistent with the received selection input. The method may include, before presenting the listing of potential problems, presenting visual indicia indicative of potential problems having been identified. The signals may comprise information consistent with the HL7 or Clinical Document Architecture standard. The method may include updating a patient's electronic health record consistent with the selection input. Automatically reviewing patient encounter-related information may comprise reviewing, with an NLP engine, encounter related information associated with a patient and identifying, by a problem list identification engine, potential problems associated with the patient. The method may include receiving validation-related user input from the user. The validation-related user input indicates the user accepts the listing of potential problems as being representative of the patient's current problems. The method may include receiving edit input from the user, related to at least one of the potential problems. The edit input may comprise an indication from the user that at least one of the potential problems be eliminated from the listing of potential problems. The method may include generating a response document consistent with the selection input, the response document memorializing the validation of a potential problem. The method may include receiving from the user modification input, modification input resulting in at least one of the identified problems being changed or eliminated. Systems and devices may perform these methods.

Unless otherwise indicated, all numbers expressing quantities, measurement of properties, and so forth used in the specification and claims are to be understood as being modified by the term "about". Accordingly, unless indicated to the contrary, the numerical parameters set forth in the specification and claims are approximations that can vary depending on the desired properties sought to be obtained by those skilled in the art utilizing the teachings of the present application. Not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of this disclosure are approximations, to the extent any numerical values are set forth in specific examples described herein, they are reported as precisely as reasonably possible. Any numerical value, however, may well contain errors associated with testing or measurement limitations.

The techniques of this disclosure may be implemented in a wide variety of computer devices, such as one or more servers, laptop computers, desktop computers, notebook computers, tablet computers, hand-held computers, smart phones, or any combination thereof. Any components, modules or units have been described to emphasize functional aspects and do not necessarily require realization by one or more different hardware units.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to server 4030, repository 4040, computing device 4010, other systems and devices described herein, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between server 4030 and/or client computing device 4010. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The methods thus described may be implemented on one or more computing systems having processors and memories. Non-transient computer readable media may also include instructions that cause such systems to carry out methods described above. The term "non-transitory" (or non-transient) may indicate that the storage medium is not embodied in a carrier wave or a propagated signal. In certain examples, a non-transitory storage medium may store data that can, over time, change (e.g., in RAM or cache).

What is claimed is:

1. A computer-implemented method for determining insufficient medical information associated with a patient, the method comprising:
    receiving, by a computing device, documentation comprising a plurality of documented items related to the patient;
    identifying, by the computing device, a case model associated with the patient;
    mapping, by the computing device, using a natural language processing (NLP) engine, the documented items of the documentation to corresponding items of the case model;
    mapping, by the computing device and using the NLP engine, each of the documented items to an intermediary code set comprising one or more concept identification codes included in the case model associated with the patient;
    determining, by the computing device and using the NLP engine, based on the mapping to the intermediary code set included in the case model, that each respective documented item of the documented items is one of (i) relevant, or (ii) historical;
    limiting, by the computing device, the mapping of the documented items of the documentation to relevant documented items of the documented items as determined based on the mapping to the intermediary code set included in the case model;
    determining, by the computing device and based on the mapping performed using the NLP engine, one or more undocumented items such that the one or more undocumented items define a medical concept missing from the documentation, such that the one or more undocumented items, in combination with the relevant documented items, complete one or more of a medical diagnosis, a medical condition, or a medical procedure associated with the patient;
    generating, by the computing device and based on the one or more undocumented items, a code representative of the one or more undocumented items that define the medical concept missing from the documentation; and
    outputting, by the computing device, the code representative of the one or more undocumented items that define the medical concept missing from the documentation.

2. The computer-implemented method of claim 1, wherein mapping the documented items of the documentation to the corresponding items of the case model comprises comparing, by the computing device and using the NLP engine, the plurality of documented items to items predetermined for the patient and included in the case model.

3. The computer-implemented method of claim 1, wherein:
    the medical concept is one of a plurality of medical concepts associated with the patient,
    the one or more undocumented items comprise a plurality of undocumented items, and
    each of the plurality of undocumented items is associated with a different one of the plurality of medical concepts associated with the patient.

4. The computer-implemented method of claim 1, wherein:
the medical concept is a first medical concept,
at least one of the one or more undocumented items links a second medical concept and a third medical concept to the first medical concept, and
the second medical concept and the third medical concepts are defined by at least some of the plurality of documented items.

5. The computer-implemented method of claim 1, wherein at least one of the one or more undocumented items confirms the medical concept, and wherein the medical concept was previously indicated and unconfirmed by the subset of the plurality of documented items.

6. The computer-implemented method of claim 1, further comprising, responsive to receiving the code, generating, based on the code and for display, a query presenting at least one of the one or more undocumented items for selection.

7. The computer-implemented method of claim 1, further comprising outputting, by the computing device, a computer-assisted physician documented (CAPD) query associated with the one or more undocumented items that define the medical concept missing from the documentation, the CAPD query being compliant with automated clinical documentation (ACDI) technology.

8. The computer-implemented method of claim 1, further comprising obtaining, by the computing system, the one or more concept identification codes of the intermediary code set from a healthcare data dictionary (HDD).

9. The computer-implemented method of claim 8, wherein each respective concept identification code of the intermediary code set conforms to at least one of an International Classification of Diseases (ICD)-9 standard, an ICD-10 standard, or a Systematized Nomenclature of Medicine-Clinical Terms (SNOMED-CT) standard.

10. A computerized system for coding medical documentation, the computerized system comprising one or more computing devices configured to:
receive documentation comprising a plurality of documented items related to the patient;
identify a case model associated with the patient;
use a natural language processing (NLP) engine to map the documented items of the documentation to corresponding items of the case model;
use the NLP engine to map each of the documented items to an intermediary code set comprising one or more concept identification codes included in the case model associated with the patient;
use the NLP engine to determine, based on the mapping to the intermediary code set included in the case model, that each respective documented item of the documented items is one of (i) relevant, or (ii) historical;
limit the mapping of the documented items of the documentation to relevant documented items of the documented items as determined based on the mapping to the intermediary code set included in the case model;
determine, based on the mapping performed by the NLP engine, one or more undocumented items such that the one or more undocumented items define a medical concept missing from the documentation, such that the one or more undocumented items, in combination with the relevant documented items, complete one or more of a medical diagnosis, a medical condition, or a medical procedure associated with the patient;
generate, based on the one or more undocumented items, a code representative of the one or more undocumented items that define the medical concept missing from the documentation; and
output the code representative of the one or more undocumented items that define the medical concept missing from the documentation.

11. The computerized system of claim 10, wherein to invoke the NLP engine to map the documented items of the documentation to the corresponding items of the case model, the one or more computing devices are configured to invoke the NLP engine to compare the plurality of documented items to items predetermined for the patient and included in the case model.

12. The computerized system of claim 10, wherein:
the medical concept is one of a plurality of medical concepts associated with the patient,
the one or more undocumented items comprise a plurality of undocumented items, and each of the plurality of undocumented items is associated with a different one of the plurality of medical concepts associated with the patient.

13. The computerized system of claim 10, wherein:
the medical concept is a first medical concept,
at least one of the one or more undocumented items links a second medical concept and a third medical concept to the first medical concept, and
the second medical concept and the third medical concepts are defined by at least some of the plurality of documented items.

14. The computerized system of claim 10, wherein at least one of the one or more undocumented items confirms the medical concept, and wherein the medical concept was previously indicated and unconfirmed by the subset of the plurality of documented items.

15. The computerized system of claim 10, wherein the one or more computing devices are configured to, responsive to receiving the code, generate, based on the code and for display, a query presenting at least one of the one or more undocumented items for selection.

16. The computerized system of claim 10, wherein the one or more computing devices comprise a documentation insufficiency coding engine.

17. The computerized system of claim 10, wherein the one or more computing devices are configured to output a computer-assisted physician documented (CAPD) query associated with the one or more undocumented items that define the medical concept missing from the documentation, the CAPD query being compliant with automated clinical documentation (ACDI) technology.

18. The computerized system of claim 10, wherein the one or more computing devices are configured to obtain the one or more concept identification codes of the intermediary code set from a healthcare data dictionary (HDD).

19. A non-transitory computer-readable storage medium storing instructions that, when executed, cause one or more processors to:
receive documentation comprising a plurality of documented items related to the patient;
identify a case model associated with the patient;
use a natural language processing (NLP) engine to map the documented items of the documentation to corresponding items of the case model;
use the NLP engine to map each of the documented items to an intermediary code set comprising one or more concept identification codes included in the case model associated with the patient;

use the NLP engine to determine, based on the mapping to the intermediary code set included in the case model, that each respective documented item of the documented items is one of (i) relevant, or (ii) historical;
limit the mapping of the documented items of the documentation to relevant documented items of the documented items as determined based on the mapping to the intermediary code set included in the case model;
determine, based on the mapping performed by the NLP engine, one or more undocumented items such that the one or more undocumented items define a medical concept missing from the documentation, such that the one or more undocumented items, in combination with the relevant documented items, complete one or more of a medical diagnosis, a medical condition, or a medical procedure associated with the patient;
generate, based on the one or more undocumented items, a code representative of the one or more undocumented items that define the medical concept missing from the documentation; and
output the code representative of the one or more undocumented items that define the medical concept missing from the documentation.

20. The non-transitory computer-readable storage medium of claim 19, wherein the instructions that cause the one or more processors to invoke the NLP engine to map the documented items of the documentation to the corresponding items of the case model comprise instructions that, when executed, cause the one or more processors to invoke the NLP engine to compare the plurality of documented items to items predetermined for the patient and included in the case model.

21. The non-transitory computer-readable storage medium of claim 19, further storing instructions that cause the one or more processors to, responsive to receiving the code, generate, based on the code and for display, a query presenting at least one of the one or more undocumented items for selection.

* * * * *